US009502658B2

(12) United States Patent
Jackson et al.

(10) Patent No.: US 9,502,658 B2
(45) Date of Patent: Nov. 22, 2016

(54) FULLERENE DERIVATIVES AND RELATED MATERIALS, METHODS, AND DEVICES

(71) Applicants: Nano-C, Inc., Westwood, MA (US); Merck Patent GmbH, Darmstadt (DE)

(72) Inventors: Edward A. Jackson, Ayer, MA (US); Henning Richter, Newton, MA (US); Nicolas Blouin, Southampton (GB); Stéphane Berny, Southampton (GB)

(73) Assignees: NANO-C, INC., Westwood, MA (US); MERCK PATENT GMBH, Darmstadt (DE)

( * ) Notice: Subject to any disclaimer, the term of this patent is extended or adjusted under 35 U.S.C. 154(b) by 179 days.

(21) Appl. No.: 14/257,223

(22) Filed: Apr. 21, 2014

(65) Prior Publication Data
US 2014/0312281 A1    Oct. 23, 2014

Related U.S. Application Data

(63) Continuation of application No. PCT/EP2014/000793, filed on Mar. 24, 2014.

(60) Provisional application No. 61/814,709, filed on Apr. 22, 2013, provisional application No. 61/869,460, filed on Aug. 23, 2013.

(51) Int. Cl.
| | |
|---|---|
| H01B 1/00 | (2006.01) |
| H01L 51/00 | (2006.01) |
| C01B 31/00 | (2006.01) |
| H01B 1/04 | (2006.01) |
| C01B 31/02 | (2006.01) |
| C07C 13/64 | (2006.01) |
| H01L 51/42 | (2006.01) |

(52) U.S. Cl.
CPC ....... *H01L 51/0047* (2013.01); *C01B 31/0213* (2013.01); *C07C 13/64* (2013.01); *H01B 1/04* (2013.01); *C07C 2104/00* (2013.01); *H01L 51/0035* (2013.01); *H01L 51/0043* (2013.01); *H01L 51/4253* (2013.01); *Y02E 10/549* (2013.01)

(58) Field of Classification Search
CPC ...... H01B 1/00; H01B 1/04; C07C 2104/00; B82Y 30/00; B82Y 40/00; C01B 31/0213
See application file for complete search history.

(56) References Cited

U.S. PATENT DOCUMENTS

| | | | |
|---|---|---|---|
| 5,763,719 A | 6/1998 | Gugel et al. | |
| 8,440,109 B2 * | 5/2013 | Itoh | B82Y 10/00 252/500 |
| 8,697,988 B2 | 4/2014 | Laird et al. | |
| 8,715,606 B2 | 5/2014 | Laird et al. | |
| 8,741,448 B2 * | 6/2014 | Chen | C07D 409/10 257/40 |
| 9,156,696 B2 * | 10/2015 | Dong | C07C 17/16 |
| 2010/0132782 A1 | 6/2010 | Laird et al. | |
| 2012/0004476 A1 | 1/2012 | Yoon et al. | |

FOREIGN PATENT DOCUMENTS

| | | |
|---|---|---|
| DE | 43 01 458 A1 | 7/1994 |
| DE | 4301458 A | 7/1994 |
| JP | 2011-238847 A | 11/2011 |
| JP | 2013-128001 A | 6/2013 |
| WO | WO 94/017018 A | 8/1994 |

OTHER PUBLICATIONS

Zhang et al "Reaction of C60 with benzocyclobutenol . . . ", J. Org. Chem. 1994, 59, 5235-38.*
Kraus et al "Covalent attachment of various substituents in closest proximity to the C60 core . . . ", Tetrahydron, vol. 51, No. 36, pp. 9927-9940 (1995).*
Belik et al., "Reaction of Buckminsterfullerene with ortho-Quincdimethane: a New Access to Stable $C_{60}$ Derivatives", Angew. Chem. Int. Ed. Engl., 1993, 32, No. 1,. pp. 78-80.
Lu et al.; "Co-Catalyzed Radical Cycloaddition of [60]Fullerene with Active Dibromides: Selective Synthesis of Carbocycle-Fused Fullerene Monoadducts", Organic Letters, Am. Chem. Soc., DOI 10.1021/ol401876n (Jul. 4, 2013).
Voroshazi et al., "Novel bis-$C_{60}$derivative compared to other fullerene bis-adducts in high efficiency polymer photovoltaic cells". J. Material Chem., DOI: 10.1039/c1jm12307f. (May 24, 2011).
International Search Report received in connection with international application No. PCT/EP2014/000793, dated Oct. 6, 2014.
Chuang et al., "Approaches to open fullerenes: synthesis and kinetic stability of Diels-Alder adducts of substituted isobenzofurans and C60", Journal of Organic Chemistry vol. 72, 2007, pp. 2716-2723.
Lamparth et al: "Reversible Template-Directed Activation of Equatorial Double Bonds of the Fullerene Framework: Regioselective Direct Synthesis, Crystal Structure and Aromatic Properties of Th-C66 (C00Et) 12", Angew. Chem. Int. Ed. Engl ., vol. 34(15), 1995, pp. 1607-1609.
Kräutler et al: "Efficient preparation of monoadducts of (60) fullerene and anthracenes by solution chemistry and their thermolytic decomposition in the solid state", Chemistry—A European Journal, vol. 7(15), 2001, pp. 3223-3235.
Murata et al., "Synthesis and reaction of fullerene C70 encapsulating two molecules of H2", Journal of the American Chemical Society, vol. 130, 2008, pp. 15800-15801.

(Continued)

*Primary Examiner* — Mark Kopec
(74) *Attorney, Agent, or Firm* — The Marbury Law Group, PLLC

(57) ABSTRACT

The invention relates to improved fullerene derivatives, to methods for their synthesis and any educts or intermediates used in such methods, to compositions and formulations containing fullerene derivatives, to the use of the fullerene derivatives, compositions and formulations in, or for the preparation of, organic electronic (OE) devices like for example organic photovoltaic (OPV) devices or organic photodetectors (OPD), and to OE, OPV and OPD devices comprising, or being prepared from, these fullerene derivatives, compositions or formulations.

31 Claims, No Drawings

(56) References Cited

OTHER PUBLICATIONS

Database WPI, Week 201349, Thomson Scientific. London. GB, AN 2013-L37915, XP002729432. & JP 2013 128001 A (Mitsubishi Chem Corp), Jun. 27, 2013 (Jun. 27, 2013), abstract.
Database WPI, Week 201180, Thomson Scientific. London. GB; AN 2011-P40096, XP002729428. & JP 2011 238847 A (Mitsubishi Chem Corp), Nov. 24, 2011 (Nov. 24, 2011), abstract.
Chuang et al., "Approaches to Open Fullerenes: Synthesis and Kinetic Stability of Diels-Alder Adducts of Substituted Isobenzofurans and $C_{60}$", J. Org. Chem., vol. 72, pp. 2716-2723, (2007).
He et al., "High performance low band gap polymer solar cells with a non-conventional acceptor", Chem. Commun., vol. 48, pp. 7616-7618 (2012).
He et al., "Novel fullerene acceptors: synthesis and application in low band gap plolymer solar cells", J. Mater. Chem., DOI: 10.1039/c2jm31712e, (2012) (4 pgs.).

* cited by examiner

FULLERENE DERIVATIVES AND RELATED MATERIALS, METHODS, AND DEVICES

CROSS REFERENCE TO RELATED APPLICATIONS

This application claims benefit of U.S. Provisional Application Ser. No. 61/814,709, filed Apr. 22, 2013, and U.S. Provisional Application Ser. No. 61/869,460, filed Aug. 23, 2013. This application also claims priority to international application no. PCT/EP2014/000793, filed Mar. 24, 2014. The disclosures of the aforementioned applications are incorporated herein by reference in their entireties.

TECHNICAL FIELD

The invention relates to improved fullerene derivatives, to methods for their synthesis and any educts or intermediates used in such methods, to compositions and formulations containing fullerene derivatives, to the use of the fullerene derivatives, compositions and formulations in, or for the preparation of, organic electronic (OE) devices like for example organic photovoltaic (OPV) devices or organic photodetectors (OPD), and to OE, OPV and OPD devices comprising, or being prepared from, these fullerene derivatives, compositions or formulations.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The organic semiconducting materials are typically present in the electronic device in the form of a thin layer, for example of between 50 and 300 nm thickness.

The photosensitive layer in an OPV or OPD device is typically composed of at least two materials, a p-type semiconductor such as a polymer, an oligomer or a defined molecular unit, and a n-type semiconductor which is for example a fullerene derivative.

Fullerene derivatives are known in the art. See for example Hirsch, Brettreich, *Fullerenes: Chemistry and Reactions*, Wiley, 2005. See also for example E. Voroshazi et al., *J. Mater. Chem.* 2011, 21, 17345-17352; K.-H. Kim et al., *Chem. Mater.* 2011, 23, 5090-5095; and X. Meng, *ACS Appl. Mater. Interfaces* 2012, 4, 5966-5973. See also US 2010/0132782 A1, US 2012/0004476 A1, WO 2008/018931 A1, WO 2010/087655 A1 and U.S. Pat. No. 8,217,260, which disclose o-QDM (ortho-quinodimethane) fullerenes.

However, while in recent years many p-type semiconductors, mainly polymers, have been prepared to enhance the performance of an OPV device, the development of suitable fullerene derivatives for use as n-type semiconductor in OPV devices has been limited to only a few selected candidates like PCBM-$C_{60}$. Also, the physical properties of the fullerene derivatives known in the art, such as solubility, light stability, thermal stability are limiting their use in commercial applications.

Thus there is still a need for fullerene derivatives which are easy to synthesize, especially by methods suitable for mass production, show good structural organization and film-forming properties, exhibit good electronic properties, especially a high charge carrier mobility, a good processability, especially a high solubility in organic solvents, and high light and thermal stability.

It was an aim of the present invention to provide fullerene derivatives that provide one or more of the above-mentioned advantageous properties. Another aim of the invention was to extend the pool of n-type OSC materials available to the expert. Other aims of the present invention are immediately evident to the expert from the following detailed description.

The inventors of this invention have found that one or more of the above aims can be achieved by providing fullerene derivatives as claimed hereinafter. These fullerene derivatives are based on o-QDM fullerene, which is substituted in both alpha-positions to the benzene ring.

It was found that the fullerene derivatives as claimed hereinafter demonstrate one or more of the improved properties as described above, especially for use in OPV/OPD applications, and are better suitable for use as n-type semiconductor in OE devices compared to the fullerene derivatives as disclosed in prior art.

U.S. Pat. No. 5,763,719 and DE 4301458 A1 disclose an o-QDM fullerene of the following formula

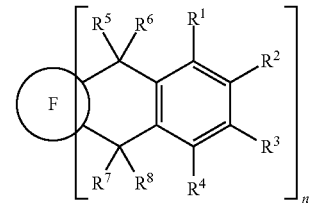

wherein "F" is a fullerene and $R^1$ to $R^8$ denote a H-atom or a substituent selected from a broad variety of meanings.

JP 2013-128001 A1 and JP 2011-238847 A1 disclose an o-QDM fullerene derivative of the following formula

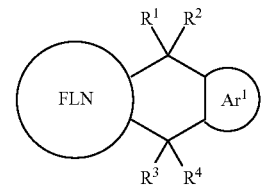

wherein "FLN" is a fullerene, $Ar^1$ is an aryl group and $R^1$ to $R^4$ denote a H-atom or a substituent selected from a broad variety of meanings. Again, there is only explicit written disclosure for fullerenes, and their synthesis, wherein all of $R^1$ to $R^4$ denote H.

S. Lu et al., *Org. Letters* 2013, disclose an o-QDM fullerene derivative of the following formula

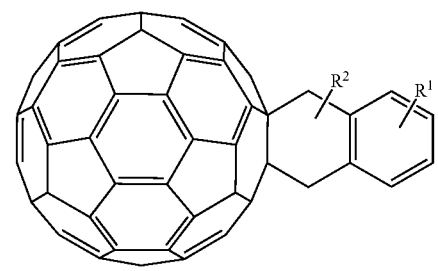

wherein $R^2$ is methyl and $R^1$ is for example $COOCH_3$ or CN.

Youjun He et al., *J. Mater. Chem.* 2012, 22, 13391, disclose o-QDM fullerene derivatives of the following formulae

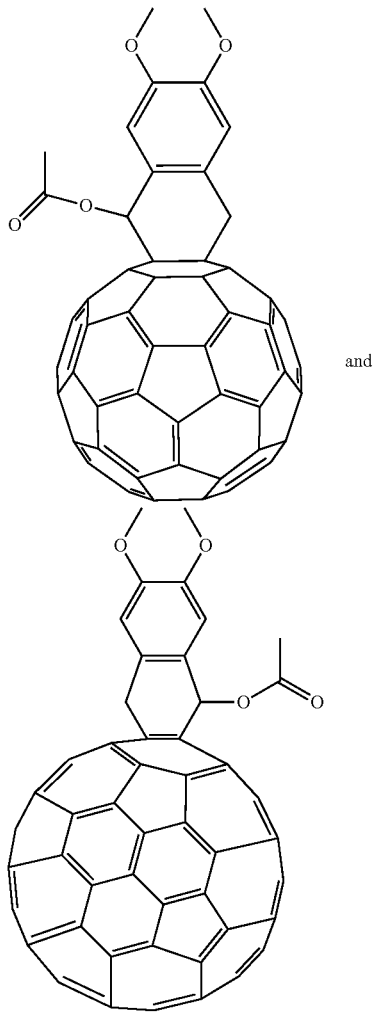

and

However, fullerene derivatives as claimed hereinafter have hitherto not been disclosed or suggested in prior art.

SUMMARY

The invention relates to compounds of formula I, including isomers thereof

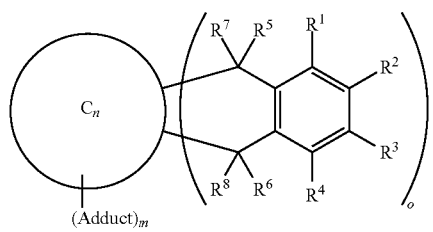

I wherein $C_n$ is a fullerene composed of n carbon atoms, optionally with one or more atoms trapped inside, Adduct is a secondary adduct, or a combination of secondary adducts, appended to the fullerene $C_n$, m is the number of secondary adducts appended to the fullerene $C_n$, and is 0, an integer $\geq 1$, or a non-integer $>0$, o is an integer $\geq 1$, $R^1$ to $R^8$ are independently of each other H, a halogen atom, or a carbyl or hydrocarbyl group having 1 to 50 C atoms, or the pair of $R^5$ and $R^6$, and/or the pair of $R^7$ and $R^8$, are covalently bonded to form a carbocyclic, heterocyclic, aromatic or heteroaromatic group having 3 to 20 ring atoms that is optionally substituted, characterized in that in formula I at least one of $R^5$ and $R^7$ is different from H and at least one of $R^6$ and $R^8$ is different from H.

The invention further relates to the use of the compounds of formula I as electron acceptor or n-type semiconductor.

The invention further relates to the use of compounds of formula I as electron acceptor or n-type component in a semiconducting material, organic electronic device or component of an organic electronic device.

The invention further relates to a composition comprising one or more compounds selected from formula I.

The invention further relates to a composition comprising two or more fullerene derivatives, one or more of which are selected from formula I.

The invention further relates to a composition comprising one or more compounds selected from formula I, preferably as electron acceptor or n-type component, and further comprising one or more semiconducting compounds, which preferably have electron donor or p-type properties.

The invention further relates to a composition comprising one or more compounds selected from formula I, and further comprising one or more p-type organic semiconductor compounds, preferably selected from conjugated organic polymers.

The invention further relates to a composition comprising one or more compounds selected from formula I, and further comprising one or more compounds which are selected from compounds having one or more of a semiconducting, charge transport, hole transport, electron transport, hole blocking, electron blocking, electrically conducting, photoconducting and light emitting property.

The invention further relates to the use of a compound selected from formula I, or a composition comprising it, as semiconducting, charge transport, electrically conducting, photoconducting or light emitting material, or in an optical, electrooptical, electronic, electroluminescent or photoluminescent device, or in a component of such a device or in an assembly comprising such a device or component.

The invention further relates to a semiconducting, charge transport, electrically conducting, photoconducting or light emitting material, which comprises a compound selected from formula I or a composition comprising it as described above and below.

The invention further relates to a formulation comprising one or more compounds selected from formula I, or a composition or material comprising it as described above and below, and further comprising one or more solvents, preferably selected from organic solvents.

The invention further relates to an optical, electrooptical, electronic, electroluminescent or photoluminescent device, or a component thereof, or an assembly comprising it, which is prepared using a formulation as described above and below.

The invention further relates to an optical, electrooptical, electronic, electroluminescent or photoluminescent device, or a component thereof, or an assembly comprising it, which comprises a compound selected from formula I, or a composition or a material comprising it as described above and below.

The optical, electrooptical, electronic, electroluminescent and photoluminescent devices include, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, laser diodes, Schottky diodes, photoconductors, photodetectors and thermoelectric device.

The components of the above devices include, without limitation, charge injection layers, charge transport layers, interlayers, planarising layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds, mixtures or materials of the present invention can be used as electrode materials in batteries and in components or devices for detecting and discriminating DNA sequences.

The invention further relates to a bulk heterojunction which comprises, or is being formed from, a composition comprising one or more compounds selected from formula I and one or more p-type organic semiconductor compounds that are selected from conjugated organic polymers. The invention further relates to a bulk heterojunction (BHJ) OPV device, or an inverted BHJ OPV device, comprising such a bulk heterojunction.

TERMS AND DEFINITIONS

As used herein, any reference to "formula I" or "formula I and its subformulae" is understood to be inclusive of any specific subformula of formula I as shown hereinafter, including but not limited to formulae I1, I2, I1a, I2a, I1a1, I1a2, I2a1 and I2a2.

As used herein, the term "fullerene" will be understood to mean a compound composed of an even number of carbon atoms, which form a cage-like fused-ring having a surface which comprises six-membered rings and five-membered rings, usually with twelve five-membered rings and the rest six-membered rings, optionally with one or more atoms trapped inside. The surface of the fullerene may also contain hetero atoms like B or N.

As used herein, the term "endohedral fullerene" will be understood to mean a fullerene with one or more atoms trapped inside.

As used herein, the term "metallofullerene" will be understood to mean an endohedral fullerene wherein the atoms trapped inside are selected from metal atoms.

As used herein, the term "carbon based fullerene" will be understood to mean a fullerene without any atoms trapped inside, and wherein the surface is comprised only of carbon atoms.

As used herein, the term "polymer" will be understood to mean a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^5$ or $R^6$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with sp$^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_W$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl or alkoxycarbonyloxy with 1 to 20 C atoms that is optionally fluorinated, X$^0$ is halogen, preferably F, Cl or Br, and R$^0$, R$^{00}$ have the meanings given above and below, and preferably denote H or alkyl with 1 to 12 C atoms.

Preferred substituents L are selected from halogen, most preferably F, or alkyl, alkoxy, oxaalkyl, thioalkyl, fluoroalkyl and fluoroalkoxy with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal CH$_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more CH$_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are C$_2$-C$_7$-1E-alkenyl, C$_4$-C$_7$-3E-alkenyl, C$_5$-C$_7$-4-alkenyl, C$_6$-C$_7$-5-alkenyl and C$_7$-6-alkenyl, in particular C$_2$-C$_7$-1E-alkenyl, C$_4$-C$_7$-3E-alkenyl and C$_5$-C$_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In an alkyl group wherein one CH$_2$ group is replaced by —O— and one CH$_2$ group is replaced by —C(O)—, these radicals are preferably neighbored. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more CH$_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one CH$_2$ group is replaced by —S—, is preferably straight-chain thiomethyl (—SCH$_3$), 1-thioethyl (—SCH$_2$CH$_3$), 1-thiopropyl (=—SCH$_2$CH$_2$CH$_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl with 1 to 15 C atoms, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloro-propionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the alkyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

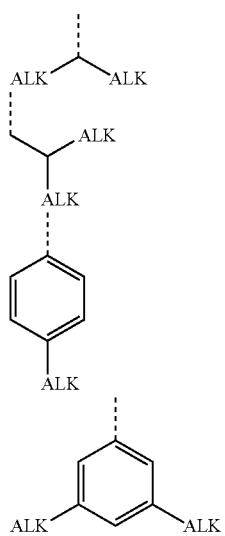

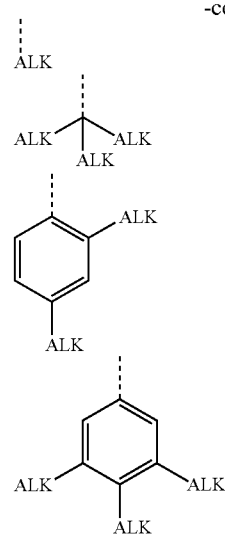

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, "halogen" or "hal" includes F, Cl, Br or I, preferably F, Cl or Br.

As used herein, —CO—, —C(=O)— and —C(O)— will be understood to mean a carbonyl group, i.e. a group having the structure

Above and below, $Y^1$ and $Y^2$ are independently of each other H, F, Cl or CN.

Above and below, $R^0$ and $R^{00}$ are independently of each other H or an optionally substituted carbyl or hydrocarbyl group with 1 to 40 C atoms, and preferably denote H or alkyl with 1 to 12 C-atoms.

DETAILED DESCRIPTION

The compounds of formula I are easy to synthesize, especially by methods suitable for mass production, and exhibit advantageous properties, for example good structural organization and film-forming properties, good electronic properties, especially high charge carrier mobility, good processability, especially high solubility in organic solvents, and high light and thermal stability.

The compounds of formula I are especially suitable as electron acceptor or n-type semiconductor, especially in semiconducting materials containing both donor and acceptor components, and for the preparation of a mixture of p-type and n-type semiconductors which are suitable for use in BHJ OPV devices and OPD devices.

For OPV and OPD application, the compounds of formula I, or a mixture comprising two or more fullerene derivatives, one or more of which are selected from formula I, is blended with a further p-type semiconductor such as a polymer, an oligomer or a defined molecular unit to form the active layer in the OPV/OPD device (also referred to as "photoactive layer").

The OPV/OPD device is usually further composed of a first, transparent or semi-transparent electrode, typically provided on a transparent or semi-transparent substrate, on one side of the active layer, and a second metallic or semi-transparent electrode on the other side of the active layer. Additional interfacial layer(s) acting as hole blocking layer, hole transporting layer, electron blocking layer and/or electron transporting layer, typically comprising a metal oxide (for example, $ZnO_x$, $TiO_x$, ZTO, $MoO_x$, $NiO_x$), a salt (example: LiF, NaF), a conjugated polymer electrolyte (for example: PEDOT:PSS or PFN), a conjugated polymer (for example: PTAA) or an organic compound (for example: NPB, $Alq_3$, TPD), can be inserted between the active layer and an electrode.

The compounds of formula I demonstrate the following improved properties compared to previously disclosed fullerene derivatives for OPV/OPD application:
1) Compared to the fullerene derivatives of the present invention, the fullerene derivatives reported in prior art, for example in US 2010/0132782 A1, US 2012/0004476 A1, WO 2008/018931 A1, WO 2010/087655 A1 and U.S. Pat. No. 8,217,260, have low solubility in solvents commonly used to prepare OPV devices.
2) The substituents $R^5$ to $R^8$ which can each possess more than one solubilising group enable higher fullerene solubility in non-halogenated solvents due to the increased number of solubilising groups.
3) Additional fine-tuning of the electronic energies (HOMO/LUMO levels), by careful selection of electron accepting and/or donating unit(s) in the positions $R^1$ of $R^8$, reduces the energy loss in the electron transfer process between the fullerene derivative and a p-type material (for example a polymer, oligomer or defined molecular unit) when used in the active layer of an OPV or OPD device.
4) Additional fine-tuning of the electronic energies (HOMO/LUMO levels), by careful selection of electron accepting and/or donating unit(s) in the positions of $R^1$ to $R^8$, increases the open circuit potential ($V_{oc}$).
5) If $R^5$ or $R^7$ and $R^6$ or $R^8$ are an alkyl chain, the fullerene solubility is greatly enhance while maintaining the HOMO position similar to the equivalent non-substituted derivatives ($R^5$ to $R^8$=H) thus increasing the open circuit potential ($V_{oc}$) of the device compared to similar device prepared using PCBM.
6) If $R^5$ or $R^7$ and $R^6$ or $R^8$ represent the same chemical entity, the resulting fullerene derivatives have a high degree of symmetry, thus increasing the probability of improving the solid state organisation of the compound while maintaining sufficient solubility in non-halogenated solvents.

In the compounds of formula I, and its subformulae as defined below, the R groups, $R^1$-$R^8$, are adapted to be distinctive structurally and provide useful properties. Moreover, the adduct groups can further provide structural distinctiveness and useful properties, when present. The value m can be, for example, 0, 1, 2 or higher for purified compounds. The value m can also be a non-integer such as, for example, 0.5 or 1.5, when mixtures of compounds are present.

The fullerene $C_n$ in formula I and its subformulae may be composed of any number n of carbon atoms. Preferably, the number n of carbon atoms of which the fullerene $C_n$ is composed is 60, 70, 76, 78, 82, 84, 90, 94 or 96, very preferably 60 or 70.

In a preferred embodiment of the present invention, n in formula I and its subformulae is 60.

In another preferred embodiment of the present invention, n in formula I and its subformulae is 70.

The fullerene $C_n$ in formula I and its subformulae is preferably selected from carbon based fullerenes, endohedral fullerenes, or mixtures thereof, very preferably from carbon based fullerenes.

Suitable and preferred carbon based fullerenes include, without limitation, $(C_{60-1h})$[5,6]fullerene, $(C_{70-D5h})$[5,6]fullerene, $(C_{76-D2*})$[5,6]fullerene, $(C_{84-D2*})$[5,6]fullerene, $(C_{84-D2d})$[5,6]fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, $Sc_3$N@$C_{80}$, $Y_3$N@$C_{80}$, $Sc_3C_2$@$C_{80}$ or a mixture of two or more of the aforementioned metallofullerenes.

In the fullerene derivatives of formula I and its subformulae, the adducts can be appended with any connectivity. The adducts are preferably appended to two different carbon atoms on the fullerene; very preferably to two different but adjacent carbon atoms on the fullerene; most preferably to two different, adjacent, five membered ring adjoining carbon atoms on the fullerene.

The fullerene $C_n$ in formula I and its subformulae is preferably substituted at a [6,6] and/or [5,6] bond, preferably substituted on at least one [6,6] bond.

The compounds of formula I and its subformulae may, in addition to the primary adduct(s) of the following structure as shown in formula I

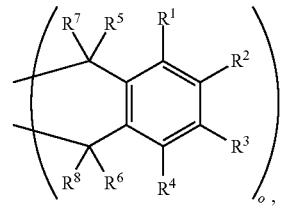

contain any number m of secondary adducts appended to the fullerene $C_n$, which are named "Adduct" in formula I and its subformulae.

The secondary adduct may be any possible adduct or combination of adducts, including o-quinonedimethane analogs, with any connectivity to the fullerene. One example of an adduct is the adduct found in PCBM, wherein the adduct can be represented by $=C(R^{31})(R^{32})$, wherein $R^{31}$ is an optionally substituted phenyl group and $R^{32}$ is $-(CH_2)COOCH_3$. $R^{31}$ can be phenyl, and n can be 3.

In the compounds of formula I and its subformulae, any adducts may be connected to one another in any combination in the finished product or during synthesis, to facilitate preferred properties in the finished product.

In the compounds of formula I and its subformulae, the number m of secondary adducts appended to the fullerene $C_n$ is 0, an integer ≥1, or a non-integer >0 like 0.5 or 1.5, and is preferably 0, 1, 2 or 3, very preferably 0, 1 or 2.

In a preferred embodiment of the present invention, m in formula I and its subformulae is 0.

In another preferred embodiment, the compound of formula I and its subformulae is free of any secondary ortho-quinodimethane fullerene adduct including the Adduct shown in formula I.

In another preferred embodiment of the present invention, m in formula I and its subformulae is 1, 2 or 3.

The secondary adduct, named "Adduct" in formula I and their subformulae, is preferably selected from the following formulae

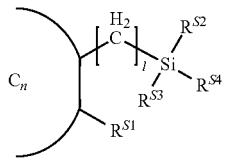

S-1

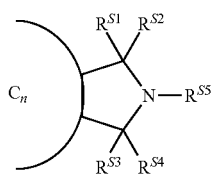

S-2

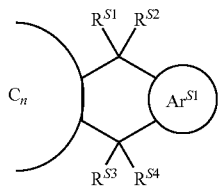

S-3

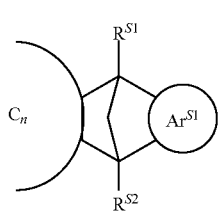

S-4

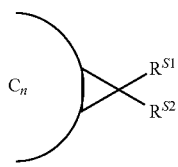

S-4

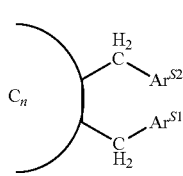

S-5

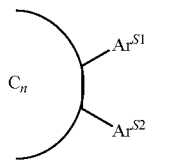

S-6

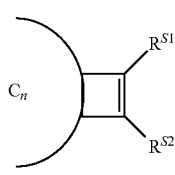

S-7

-continued

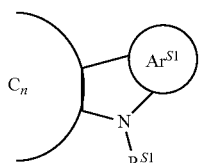

S-8

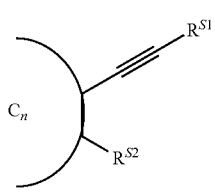

S-9 wherein $R^{S1}$, $R^{S2}$, $R^{S3}$, $R^{S4}$ and $R^{S5}$ independently of each other denote H, halogen or CN, or have one of the meanings of $R^1$ as given above or one of the meanings of $Ar^{S1}$, and $Ar^{S1}$ and $Ar^{S2}$ independently of each other denote an aryl or heteroaryl group with 5 to 20, preferably 5 to 15, ring atoms, which is mono- or polycyclic, and which is substituted by one or more identical or different substituents $R^S$, wherein $R^S$ denotes halogen, preferably F, or a straight-chain, branched or cyclic alkyl moiety with 1 to 30, preferably 4 to 20, very preferably 5 to 15, C atoms, in which one or more $CH_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, and R$^0$ and R$^{00}$ have one of the meanings given above and below, and preferably denote H or alkyl with 1 to 12 C-atoms.

In another preferred embodiment of the present invention, m in formula I and its subformulae is 1, 2 or 3, and the Adduct is selected from formulae S1 to S9 as defined above.

$R^1$ to $R^8$ in formula I and its subformulae preferably denote H, halogen, or a straight-chain, branched or cyclic alkyl group with 1 to 50 C atoms, in which one or more $CH_2$ groups are optionally replaced by —O—, —S—, —C(=O)—, —C(=S)—, —C(=O)—O—, —O—C(=O)—, —S(O)$_2$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, or one or more $CH_2$ or $CH_3$ groups are replaced by a cationic group or an anionic group, and in which one or more H atoms are optionally replaced by F, Cl, Br, I or CN, or $R^1$ to $R^8$ denote a non-aromatic carbo- or heterocyclic group that is saturated or unsaturated, or an aryl group or heteroaryl group, wherein each of the aforementioned cyclic groups has 3 to 20, preferably 5 to 15, ring atoms, is mono- or polycyclic, contains fused and/or unfused rings, and is optionally substituted by one or more groups $R^S$, wherein $R^S$ has one of the meanings of L as given above, and preferably denotes halogen, very preferably F, or a straight-chain, branched or cyclic alkyl moiety with 1 to 30, preferably 4 to 20, very preferably 5 to 15, C atoms, in which one or more $CH_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, and R$^0$ and R$^{00}$ have one of the meanings given above and below, and preferably denote H or alkyl with 1 to 12 C-atoms.

In formula I and its subformulae preferably one or more of $R^1$, $R^2$, $R^3$, $R^4$, $R^5$, $R^6$, $R^7$ and $R^8$ denote H.

Further preferably one or more of $R^1$, $R^2$, $R^3$, $R^4$, $R^5$, $R^6$, $R^7$ and $R^8$ denote halogen, or a straight-chain, branched or cyclic alkyl group with 1 to 50, preferably 2 to 50, more preferably 2 to 25, most preferably 2 to 12, C-atoms, in which one or more $CH_2$ groups are optionally replaced by —O—, —S—, —C(=O)—, —C(=S)—, —C(=O)—O—, —O—C(=O)—, —S(O)$_2$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, one or more $CH_2$ or $CH_3$ groups are optionally replaced by a cationic group or an anionic group, and one or more H atoms are optionally replaced by F, Cl, Br, I or CN, and wherein R$^0$ and R$^{00}$ and Y$^1$ and Y$^2$ have one of the meanings given above and below, and R$^0$ and R$^{00}$ preferably denote H or alkyl with 1 to 12 C-atoms.

Further preferably one or more of R$^1$, R$^2$, R$^3$, R$^4$, R$^5$, R$^6$, R$^7$ and R$^8$ denote an alkyl, alkoxy, thioalkyl, alkylcarbonyl, alkoxycarbonyl or alkylcarbonyloxy group, all of which are straight-chain or branched, have 2 to 20 C atoms, very preferably 2 to 12 C atoms, and are optionally fluorinated.

Further preferably one or more of R$^1$, R$^2$, R$^3$, R$^4$, R$^5$, R$^6$, R$^7$ and R$^8$ denote a non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents R$^S$ as defined above.

In formula I, preferably R$^5$ and R$^6$ are different from H and R$^7$ and R$^8$ denote H, or R$^7$ and R$^8$ are different from H and R$^5$ and R$^6$ denote H.

Preferably those of R$^5$, R$^6$, R$^7$ and R$^8$ that are different from H denote halogen or a straight-chain, branched or cyclic alkyl group with 1 to 50, preferably 2 to 50, more preferably 2 to 25, most preferably 2 to 12, C-atoms, in which one or more $CH_2$ groups are optionally replaced by —O—, —S—, —C(=O)—, —C(=S)—, —C(=O)—O—, —O—C(=O)—, —S(O)$_2$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, and wherein R$^0$ and R$^{00}$ and Y$^1$ and Y$^2$ have one of the meanings given above and below, and R$^0$ and R$^{00}$ preferably denote H or alkyl with 1 to 12 C-atoms.

In another preferred embodiment, those of R$^5$, R$^6$, R$^7$ and R$^8$ that are different from H are selected from aliphatic groups like $C_1$-$C_{50}$ optionally substituted alkyl groups, preferably longer than methyl, including $C_2$-$C_{50}$ optionally substituted alkyl groups, $C_2$-$C_{25}$ optionally substituted alkyl groups, and $C_2$-$C_{16}$ optionally substituted alkyl groups. Examples include ethyl, propyl, butyl, pentyl, hexyl, heptyl, octyl, nonyl, decyl, undecyl, dodecyl and hexadecyl including straight chain, branched and isomeric alkyl groups.

In another preferred embodiment, those of R$^5$, R$^6$, R$^7$ and R$^8$ that are different from H denote an alkyl, alkoxy, thioalkyl, alkylcarbonyl, alkoxycarbonyl or alkylcarbonyloxy group, all of which are straight-chain or branched, have 2 to 20 C atoms, very preferably 2 to 12 C atoms and are optionally fluorinated.

In another preferred embodiment one or more of R$^1$, R$^2$, R$^3$, R$^4$, R$^5$, R$^6$, R$^7$ and R$^8$ denote a straight-chain, branched or cyclic alkyl group with 1 to 50, preferably 2 to 50, more preferably 2 to 25, most preferably 2 to 12, C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms.

Further preferred cationic groups are selected from the group consisting of the following formulae

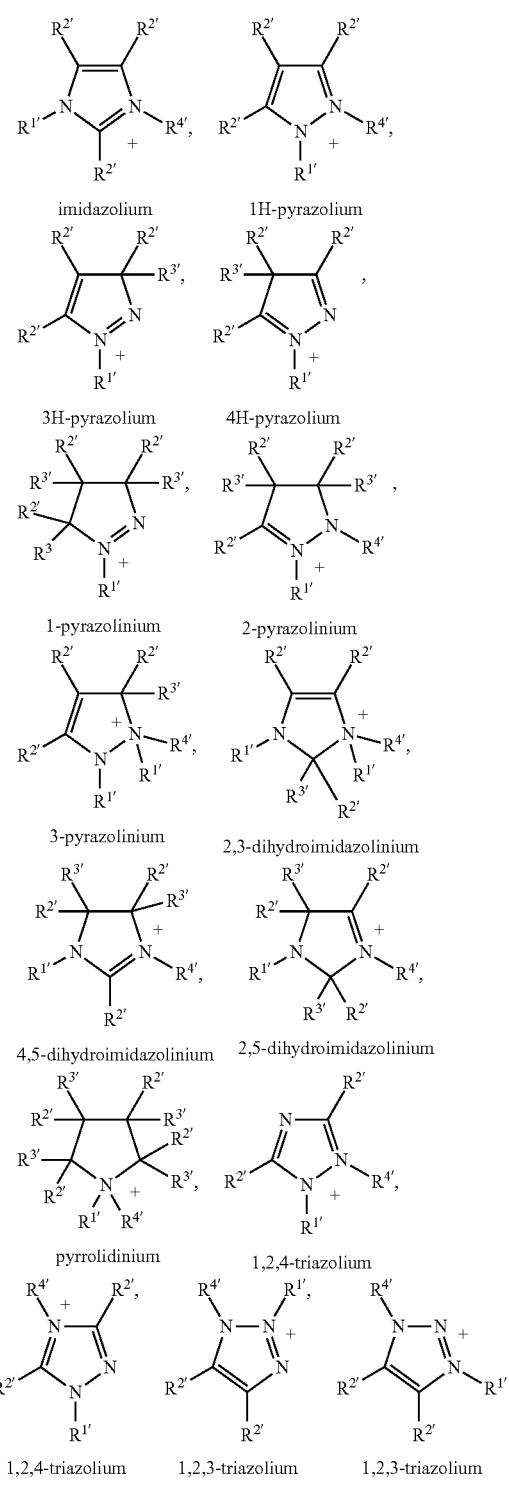

-continued

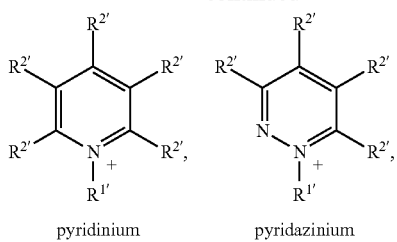

pyridinium        pyridazinium

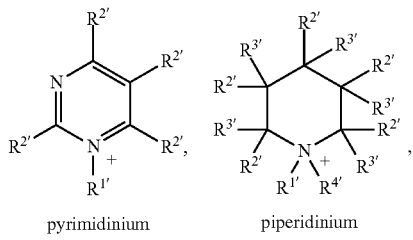

pyrimidinium      piperidinium

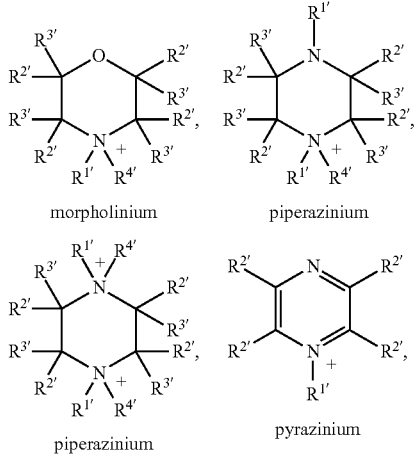

morpholinium      piperazinium

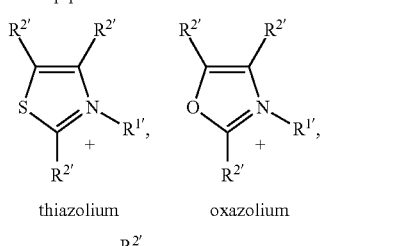

piperazinium      pyrazinium

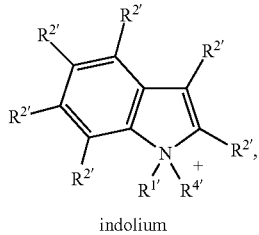

thiazolium        oxazolium

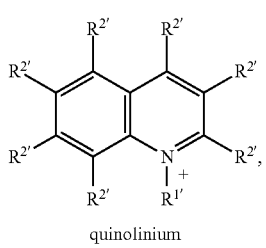

indolium

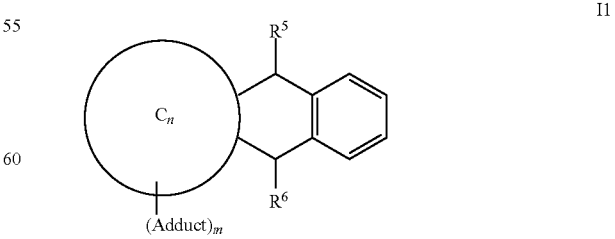

quinolinium

-continued

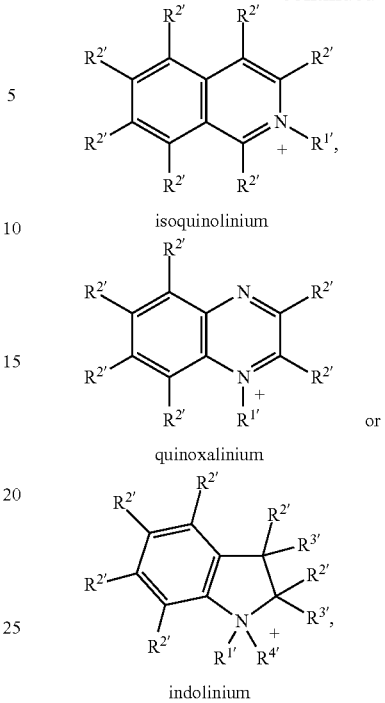

isoquinolinium quinoxalinium       or indolinium wherein $R^{1\prime}$, $R^{2\prime}$, $R^{3\prime}$ and $R^{4\prime}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents $R^S$ as defined above, or denote a link to the group $R^1$, $R^2$, $R^3$, $R^4$, $R^5$, $R^6$, $R^7$ or $R^8$, respectively.

In the above cationic groups of the above-mentioned formulae any one of the groups $R^{1\prime}$, $R^{2\prime}$, $R^{3\prime}$ and $R^{4\prime}$ (if they replace a $CH_3$ group) can denote a link to the respective group $R^1$, $R^2$, $R^3$, $R^4$, $R^5$, $R^6$, $R^7$ or $R^8$, or two neighbored groups $R^{1\prime}$, $R^{2\prime}$, $R^{3\prime}$ or $R^{4\prime}$ (if they replace a $CH_2$ group) can denote a link to the respective group $R^1$, $R^2$, $R^3$, $R^4$, $R^5$, $R^6$, $R^7$ or $R^8$.

The anionic group is preferably selected from the group consisting of borate, imide, phosphate, sulfonate, sulfate, succinate, naphthenate or carboxylate, very preferably from phosphate, sulfonate or carboxylate.

A preferred compound of formula I is selected from subformula I1

I1 wherein $C_n$, "Adduct", m, $R^5$ and $R^6$ have one of the meanings of formula I or one of the preferred meanings given above, with $R^5$ and $R^6$ being different from H.

A preferred compound of subformula I1 is selected from subformula I1a

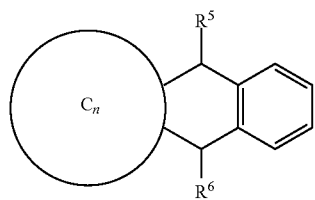
I1a wherein $C_n$, $R^5$ and $R^6$ have one of the meanings of formula I or one of the preferred meanings given above, with $R^5$ and $R^6$ being different from H.

Another preferred embodiment of the present invention relates to compounds of formula I and its subformulae, wherein the pair of $R^5$ and $R^6$ and/or the pair of $R^7$ and $R^8$, preferably only the pair of $R^7$ and $R^8$, are covalently bonded to form a carbocyclic, heterocyclic, aromatic or heteroaromatic group having 3 to 20 ring atoms that is optionally substituted.

Preferably the pair of $R^7$ and $R^8$ are covalently bonded to form a cyclic group of the formula

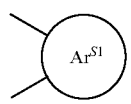

wherein $Ar^{S1}$ is as defined in formula S3 above.

Very preferably the pair of $R^7$ and $R^8$ are covalently bonded to form a cyclic group of the formula

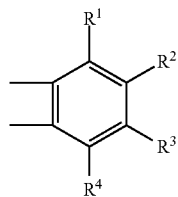

wherein $R^{1-4}$ have one of the meanings of formula I or one of the preferred meanings given above. These preferred compounds are selected from subformula I2

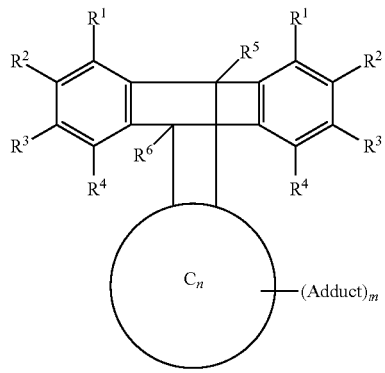
I2 wherein $C_n$, "Adduct", m, $R^{1-4}$, $R^5$ and $R^6$ have one of the meanings of formula I or one of the preferred meanings given above, and preferably $R^5$ and $R^6$ are different from H.

A preferred compound of subformula I2 is selected from subformula I2a

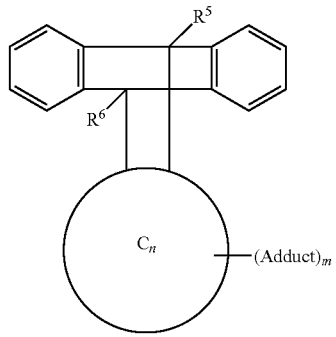
I2a wherein $C_n$, "Adduct", m, $R^5$ and $R^6$ have one of the meanings of formula I or one of the preferred meanings given above, and preferably $R^5$ and $R^6$ are different from H.

Further preferred compounds are those of the subformulae shown below.

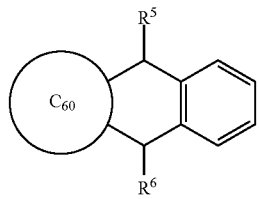
I1a1

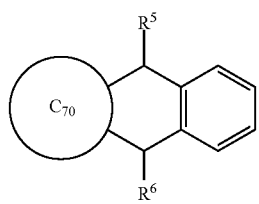
I1a2

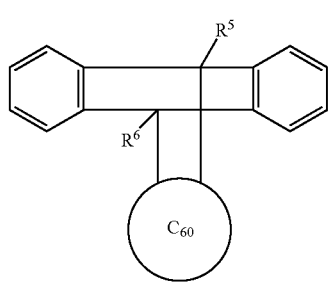
I2a1

-continued

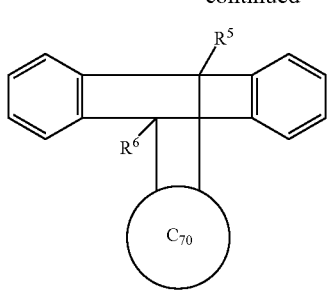

(I2a2)

wherein $R^5$ and $R^6$ denote independently of each other straight-chain or branched alkyl with 1 to 20, preferably 2 to 15 C atoms, and denote preferably ethyl, propyl, butyl, pentyl, hexyl, heptyl, octyl, nonyl, decyl, undecyl or dodecyl.

The synthesis of the compounds of formula I and its subformulae can be achieved based on method steps that individually might be known to the skilled person and described in the literature but in combination are believed novel and inventive, as will be further illustrated hereinafter.

Especially suitable and preferred synthesis methods of the compounds of formula I and its subformulae are illustrated in the synthesis schemes 1-3 shown hereinafter.

One embodiment provides, for example, a method of making a compound according to formula I comprising: reacting in one or more steps a precursor P-1 represented by P-1, wherein $R^1$ to $R^8$ have the meanings given above and below,

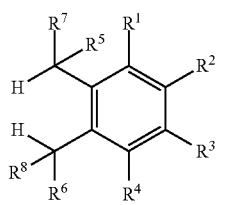

(P-1)

with at least one halogenating reagent to form a halogenated intermediate represented by P-2, wherein Hal denotes a halogen atom and $R^1$ to $R^8$ have the meanings given above and below,

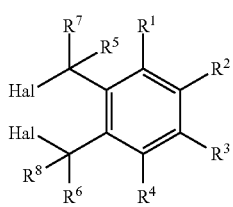

(P-2)

and
reacting the intermediate P-2 in one or more steps with a fullerene compound represented by F-1 or F-2:

(F-1)

or

(F-2)

(in other words, in F-1, m is zero), and, optionally, with a secondary adduct compound to form the compound of formula I.

These synthetic methods are further illustrated in the following synthetic schemes 1-3, wherein for the methods of making illustrated hereinbelow and hereinabove $R^1$-$R^4$ and $R^5$-$R^8$, and the fullerene compound, including $C_n$ and (adduct)$_m$ are as defined elsewhere herein. The working examples further illustrate the synthetic methods and the nature of the substituents.

In one embodiment, as described elsewhere herein, the groups $R^7$ and $R^8$ can be covalently bonded to each other to form a cyclic group, for example, a phenyl ring, as illustrated, for example, in formulae I2 and I2a.

The precursor compound P-1 can be purchased or made by methods known in the art. Working example 1.1, below, provides an example.

Halogenating reagents (or agents) are known in the art and can include fluorinating, chlorinating, brominating, and iodo reagents, (See, for example, March's Advanced Organic Chemistry, 6$^{th}$ Ed., 2007 including pages 954-964). In one embodiment, the halogenating reagent can be a bromination reagent. An example is NBS (N-Bromosuccinimide). The halogenating reagent can be selected based on its ability to halogenate selectively. As used herein, "hal" means "halogen." See working example below 1.2. For the halogenation reaction, appropriate reaction conditions such as solvent, reaction temperature, and purification methods can be used by one skilled in the art. Intermediate compound P-2 can be characterized by methods known in the art.

In a preferred embodiment, the intermediate P-2 compound is directly reacted without purification with the fullerene compound. For example, in some embodiments, purification may be attempted with use of a chromatographic medium such as untreated silica gel, but the chromatographic medium such as untreated silica gel may induce decomposition of the P-2 compound. The skilled artisan can determine whether the chromatographic medium induces decomposition. For example, the nature of the surface, morphology, particle size, and pore size can be reviewed. Decomposition may, in some cases, be a function of the surface treatment of the chromatographic medium. Silica gel and other chromatographic media can be surface functionalized as known in the art with, for example, hydrophobic moieties. For example, silica gel can be treated with pyridine. Reverse phase silica gel is known. Untreated silica gel can have a relatively polar surface compared to treated silica to increase hydrophobicity of the silica gel surface. In one embodiment, the use of untreated silica is avoided in purification of the P-2 compound before reaction of this compound with the fullerene compound. In particular, in one embodiment, the intermediate P-2 compound is directly reacted without purification with the fullerene compound. In this embodiment, solvent can be removed before reaction with fullerene. In another particular embodiment, the intermediate P-2 compound is not contacted with untreated silica gel before reacted with the fullerene compound.

For the reaction of P-2 with the fullerene compound, appropriate reaction conditions such as solvent, reaction temperature, other reagents such as crown ethers, and purification methods can be used by one skilled in the art. Working examples 1.3 and 2.1 provide preferred embodiments. The fullerene compound can either have an adduct as shown in formula I or it can be free of an adduct as shown in formula I (m=0). If the latter, an additional reaction can be carried out if desired to form the adduct substituent(s) on the fullerene. These two reaction pathways are illustrated in Scheme 1. Schemes 2 and 3 represent preferred embodiments. Therein $R^1$ to $R^4$ have the meanings given above and below and $R^9$, $R^{10}$, $R^{11}$, $R^{12}$ have the meanings given for $R^5$, $R^6$, $R^7$, $R^8$ respectively.

Scheme 1:

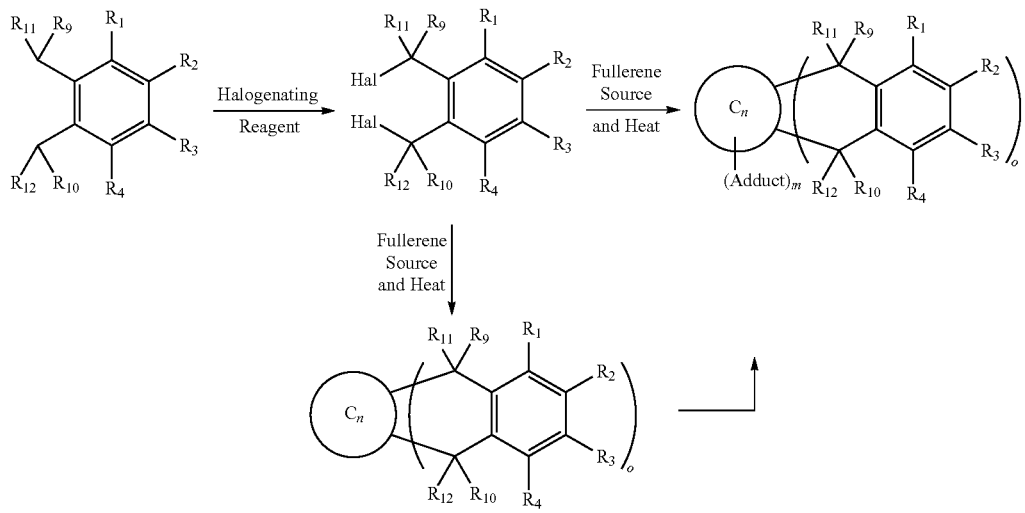

Scheme 2:

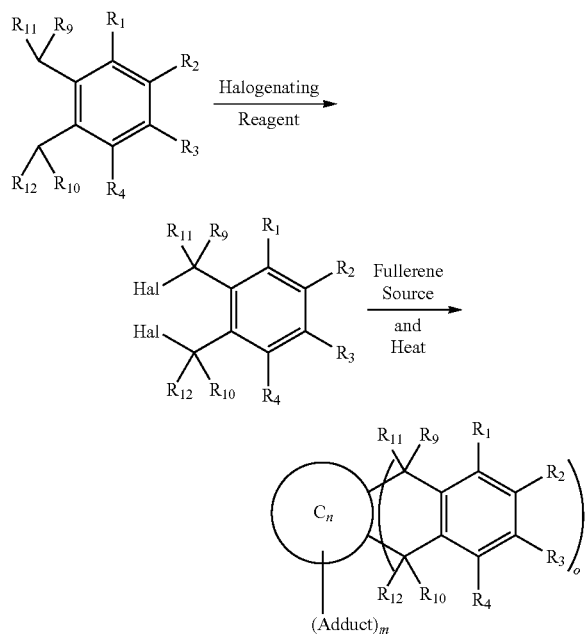

Scheme 3:

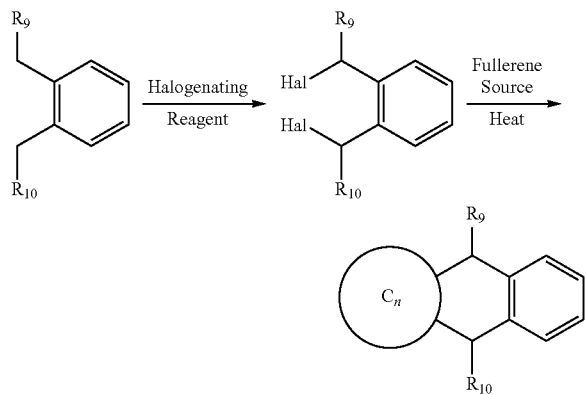

The novel methods of preparing fullerene derivatives as described above and below, and the educts and/or intermediates used therein, are another aspect of the invention.

The compounds of formula I and its subformulae can also be used in mixtures, for example together with other monomeric compounds, or polymers, having one or more of a semiconducting, charge transport, hole transport, electron transport, hole blocking, electron blocking, electrically conducting, photoconducting and light emitting property Thus, another aspect of the invention relates to a composition (hereinafter referred to as "fullerene composition"), comprising one or more fullerene derivatives selected from formula I and its subformulae or from the preferred embodiments as described above and below (hereinafter simply referred to as "fullerene derivative of this invention"), and one or more additional compounds, preferably having one or more of a semiconducting, charge transport, hole transport, electron transport, hole blocking, electron blocking, electrically conducting, photoconducting and light emitting property.

In a preferred embodiment, the composition consists essentially of, or consists of, one or more components including the compounds of formula I and its subformulae.

The additional compounds in the fullerene composition can be selected for example from fullerene derivatives other than those of this invention, or from conjugated organic polymers.

A preferred embodiment of the present invention relates to a fullerene composition, comprising one or more fullerene derivatives, at least one of which is a fullerene derivative of this invention, and further comprising one or more conjugated organic polymers, which are preferably selected from electron donor, or p-type, semiconducting polymers.

Such a fullerene composition is especially suitable for use in the photoactive layer of an OPV or OPD device. Preferably the fullerene(s) and polymer(s) are selected such that the fullerene composition forms a bulk heterojunction (BHJ).

A suitable conjugated organic polymer (hereinafter simply referred to as "polymer") for use in a fullerene composition according to the present invention can be selected from polymers as described in prior art, for example in WO/2010/008672, WO/2010/049323, WO 2011/131280, WO/2011/052709, WO/2011/052710, US/2011/0017956, WO/2012/030942 or US/8334456B2.

A preferred polymer is selected from the group consisting of poly(3-substituted thiophene) and poly(3-substituted selenophene), for example poly(3-alkyl thiophene) or poly(3-alkyl selenophene), preferably poly(3-hexyl thiophene) or poly(3-hexyl selenophene).

A further preferred polymer comprises one or more repeating units selected from formulae PIIa and PIIb:

   PIIa

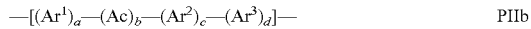   PIIb wherein
Ac is arylene or heteroarylene with 5 to 30 ring atoms that is optionally substituted by one or more groups $R^S$, and preferably has electron acceptor property,
D is arylene or heteroarylene with 5 to 30 ring atoms that is different from A, is optionally substituted by one or more groups $R^S$, and preferably has electron donor property,
$Ar^1$, $Ar^2$, $Ar^3$ are, on each occurrence identically or differently, and independently of each other, arylene or heteroarylene that is different from A and D, preferably has 5 to 30 ring atoms, and is optionally substituted, preferably by one or more groups $R^P$,
$R^P$ is on each occurrence identically or differently F, Br, Cl, —CN, —NC, —NCO, —NCS, —OCN, —SCN, —C(O)NR$^O$R$^{OO}$, —C(O)X$^O$, —C(O)R$^O$, —C(O)OR$^O$, —NH$_2$, —NR$^O$R$^{OO}$, —SH, —SR$^O$, —SO$_3$H, —SO$_2$R$^O$, —OH, —NO$_2$, —CF$_3$, —SF$_5$, optionally substituted silyl, carbyl or hydrocarbyl with 1 to 40 C atoms that is optionally substituted and optionally comprises one or more hetero atoms,
$R^O$ and $R^{OO}$ are independently of each other H or optionally substituted $C_{1-40}$ carbyl or hydrocarbyl, and preferably denote H or alkyl with 1 to 12 C-atoms,
$X^O$ is halogen, preferably F, Cl or Br,
a, b, c are on each occurrence identically or differently 0, 1 or 2,
d is on each occurrence identically or differently 0 or an integer from 1 to 10.

Preferably the polymer comprises at least one repeating unit of formula PIIa wherein b is at least 1. Further preferably the polymer comprises at least one repeating unit of formula PIIa wherein b is at least 1, and at least one repeating unit of formula PIIb wherein b is at least 1.

A further preferred polymer comprises, in addition to the units of formula PIIa and/or PIIb, one or more repeating units selected from monocyclic or polycyclic arylene or heteroarylene groups that are optionally substituted.

These additional repeating units are preferably selected of formula PIII

   PIII wherein $Ar^1$, $Ar^2$, $Ar^3$, a, c and d are as defined in formula PIIa.

$R^P$ preferably denotes, on each occurrence identically or differently, H, straight-chain, branched or cyclic alkyl with 1 to 30 C atoms, in which one or more CH$_2$ groups are optionally replaced by —O—, —S—, —C(O)—, —C(S)—, —C(O)—O—, —O—C(O)—, —NR$^O$—, —SiR$^O$R$^{OO}$—, —CF$_2$—, —CHR$^O$=CR$^{OO}$—, —CY$^1$=CY$^2$— or —C≡C— in such a manner that O and/or S atoms are not linked directly to one another, and in which one or more H atoms are optionally replaced by F, Cl, Br, I or CN, or denotes aryl, heteroaryl, aryloxy or heteroaryloxy with 4 to 20 ring atoms which is optionally substituted, preferably by halogen or by one or more of the aforementioned alkyl or cyclic alkyl groups, wherein $R^O$ and $R^{OO}$ and $Y^1$ and $Y^2$ have one of the meanings given above and below, $R^O$ and $R^{OO}$ preferably denote H or alkyl with 1 to 12 C-atoms, and $Y^1$ and $Y^2$ preferably denote F, Cl or Br.

Further preferably the polymer is selected of formula PIV:

   PIV wherein
A, B, C independently of each other denote a distinct unit of formula PIIa, PIIb or PIII,
x is >0 and ≤1,
y is ≥0 and <1,
z is ≥0 and <1,
x+y+z is 1, and
n1 is an integer >1.

Preferably at least one of B or C denotes a unit of formula PIIa. Very preferably one of B and C denotes a unit of formula PIIa and one of B and C denotes a unit of formula PIIb.

A preferred polymer of formula PIV is selected from the following formulae

   PIVa

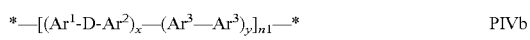   PIVb

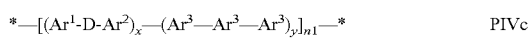   PIVc

   PIVd

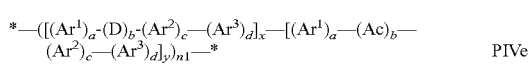   PIVe

   PIVf

   PIVg

   PIVh

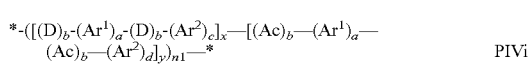   PIVi

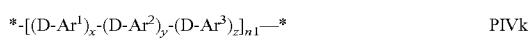   PIVk wherein D, $Ar^1$, $Ar^2$, $Ar^3$, a, b, c and d have in each occurrence identically or differently one of the meanings given in formula PIIa, Ac has on each occurrence identically or differently one of the meanings given in formula PIIb, and x, y, z and n1 are as defined in formula PIV, wherein these polymers can be alternating or random copolymers, and wherein in formula PIVd and PIVe in at least one of the repeating units $[(Ar^1)_a-(D)_b-(Ar^2)_c—(Ar^3)_d]$ and in at least one of the repeating units $[(Ar^1)_a—(Ac)_b—(Ar^2)_c—(Ar^3)_d]$ b is at least 1 and wherein in formula PIVh and PIVi in at least one of the repeating units $[(D)_b-(Ar^1)_a-(D)_b-(Ar^2)_d]$ and in at least one of the repeating units $[(D)_b-(Ar^1)_a-(D)_b-(Ar^2)_d]$ b is at least 1.

In the polymer, the total number of repeating units n1 is preferably from 2 to 10,000. The total number of repeating units n1 is preferably ≥5, very preferably ≥10, most preferably ≥50, and preferably ≤500, very preferably ≤1,000, most preferably ≤2,000, including any combination of the aforementioned lower and upper limits of n1.

The polymer can be a homopolymer or copolymer, like a statistical or random copolymer, alternating copolymer or block copolymer, or a combination of the aforementioned.

Especially preferred is a polymer selected from the following groups:

Group A consisting of homopolymers of the unit D or (Ar$^1$-D) or (Ar$^1$-D-Ar$^2$) or (Ar$^1$-D-Ar$^3$) or (D-Ar$^2$—Ar$^3$) or (Ar$^1$-D-Ar$^2$—Ar$^3$) or (D-Ar$^1$-D), i.e. where all repeating units are identical, Group B consisting of random or alternating copolymers formed by identical units (Ar$^1$-D-Ar$^2$) or (D-Ar$^1$-D) and identical units (Ar$^3$), Group C consisting of random or alternating copolymers formed by identical units (Ar$^1$-D-Ar$^2$) or (D-Ar$^1$-D) and identical units (A$^1$), Group D consisting of random or alternating copolymers formed by identical units (Ar$^1$-D-Ar$^2$) or (D-Ar$^1$-D) and identical units (Ar$^1$—Ac—Ar$^2$) or (Ac—Ar$^1$—Ac), wherein in all these groups D, Ac, Ar$^1$, Ar$^2$ and Ar$^3$ are as defined above and below, in groups A, B and C Ar$^1$, Ar$^2$ and Ar$^3$ are different from a single bond, and in group D one of Ar$^1$ and Ar$^2$ may also denote a single bond.

A preferred polymer of formula PIV and PIVa to PIVk is selected of formula PV $$R^{21}\text{-chain-}R^{22} \qquad \text{PV}$$

wherein "chain" denotes a polymer chain of formulae PIV or PIVa to PIVk, and R$^{21}$ and R$^{22}$ have independently of each other one of the meanings of R$^S$ as defined above, or denote, independently of each other, H, F, Br, Cl, I, —CH$_2$Cl, —CHO, —CR'=CR''$_2$, —SiR'R''R''', —SiR'X'X'', —SiR'R''X', —SnR'R''R''', —BR'R'', —B(OR')(OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of R$^0$ given in formula I, and two of R', R'' and R''' may also form a ring together with the hetero atom to which they are attached.

Preferred endcap groups R$^{21}$ and R$^{22}$ are H, C$_{1-20}$ alkyl, or optionally substituted C$_{6-12}$ aryl or C$_{2-10}$ heteroaryl, very preferably H or phenyl.

In the polymer represented by formula PIV, PIVa to PIVk or PV, x, y and z denote the mole fraction of units A, B and C, respectively, and n denotes the degree of polymerisation or total number of units A, B and C. These formulae includes block copolymers, random or statistical copolymers and alternating copolymers of A, B and C, as well as homopolymers of A for the case when x>0 and y=z=0.

In the repeating units and polymers of formulae PIIa, PIIb, PIII, PIV, PIVa-PIVk and PV, preferably D, Ar$^1$, Ar$^2$ and Ar$^3$ are selected from the group consisting of the following formulae

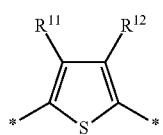
(D1)

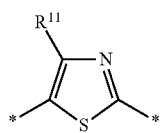
(D2)

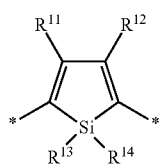
(D3)

-continued

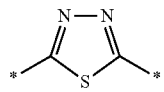
(D4)

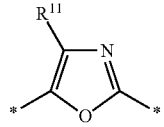
(D5)

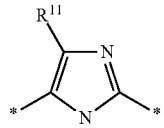
(D6)

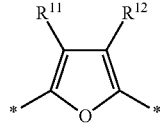
(D7)

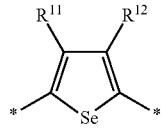
(D8)

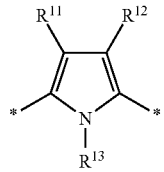
(D9)

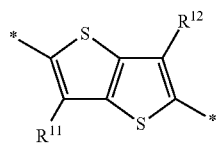
(D10)

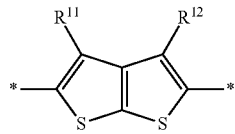
(D11)

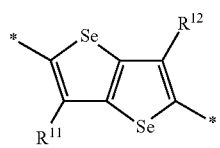
(D12)

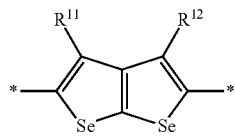
(D13)

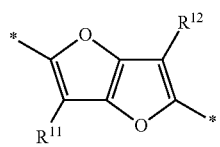
(D14)

-continued
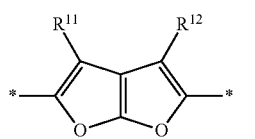 (D15)
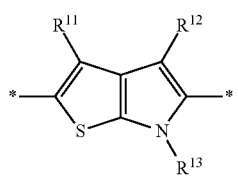 (D16)
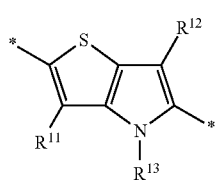 (D17)
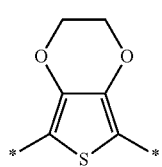 (D18)
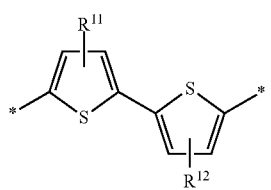 (D19)
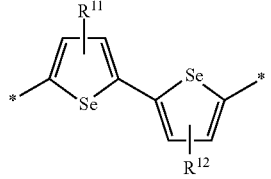 (D20)
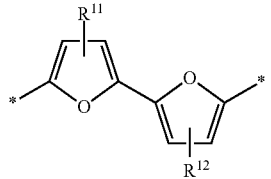 (D21)
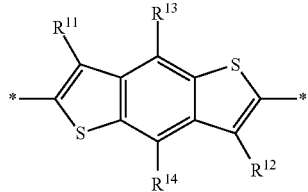 (D22)
-continued
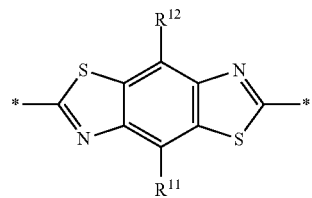 (D23)
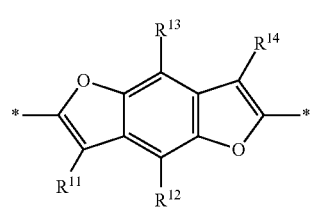 (D24)
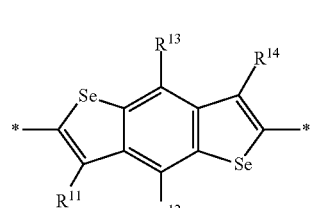 (D25)
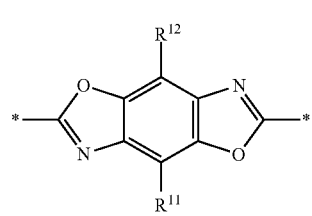 (D26)
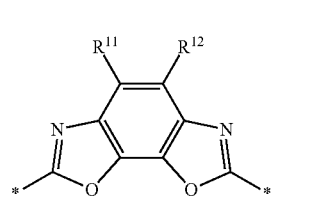 (D27)
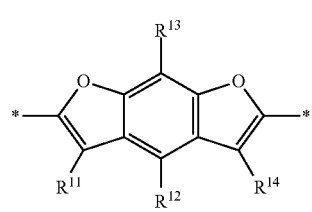 (D28)
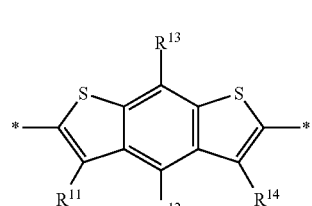 (D29)
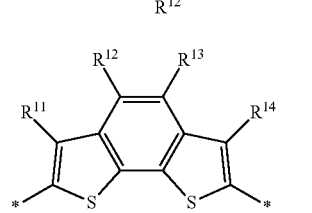 (D30)

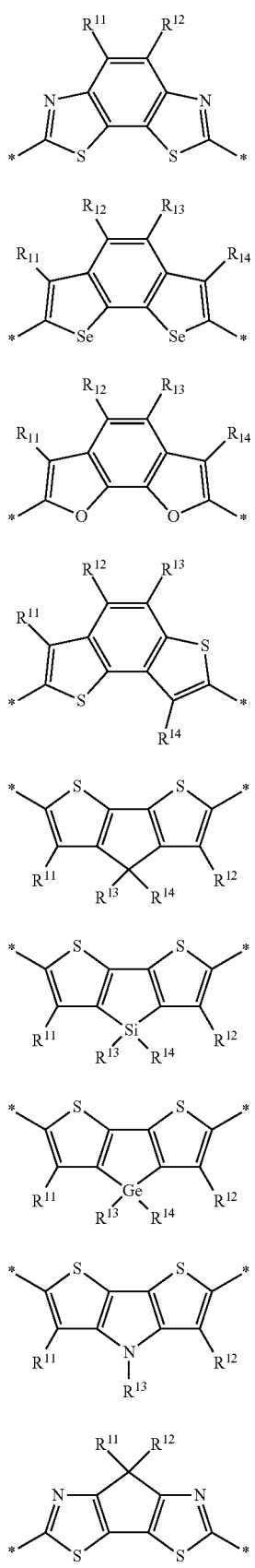
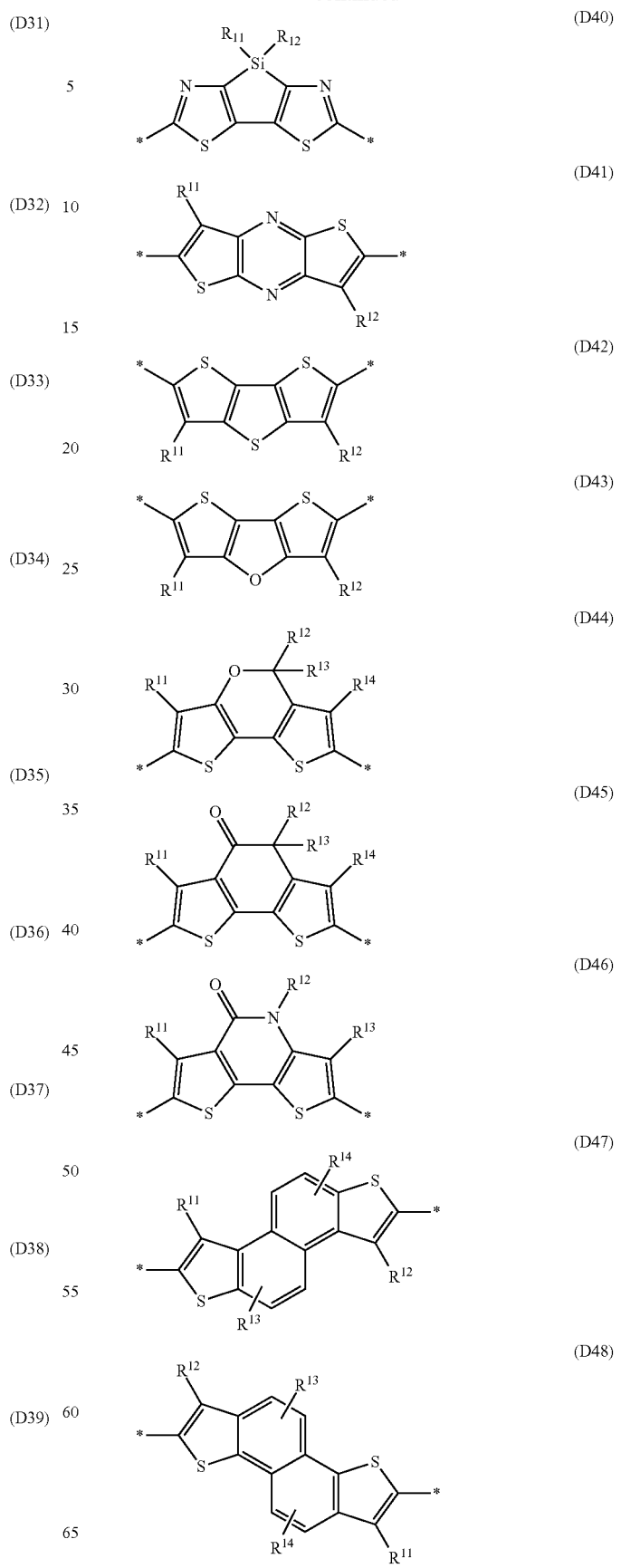

-continued
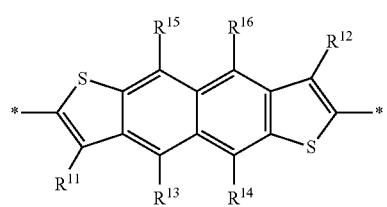
(D49)
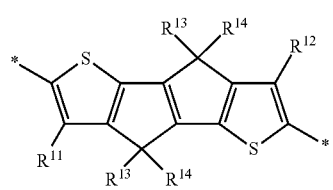
(D50)
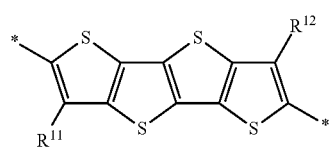
(D51)
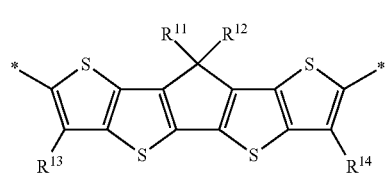
(D52)
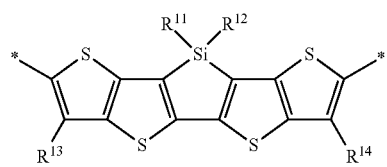
(D53)
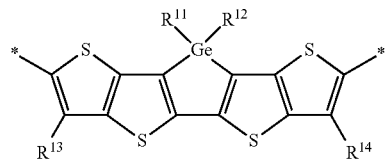
(D54)
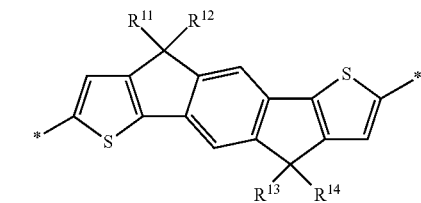
(D55)
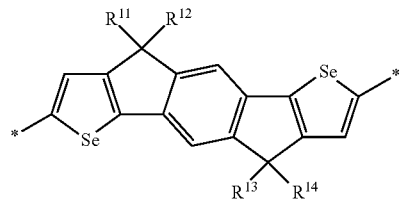
(D56)
-continued
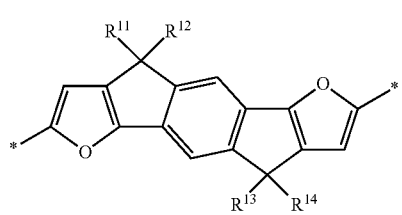
(D57)
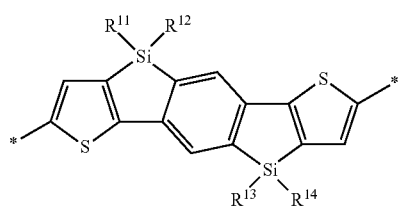
(D58)
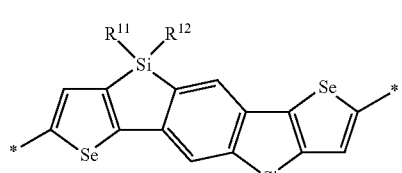
(D59)
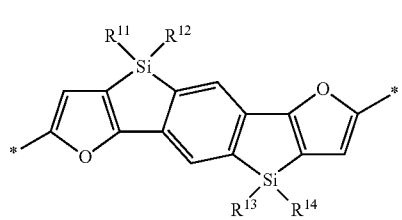
(D60)
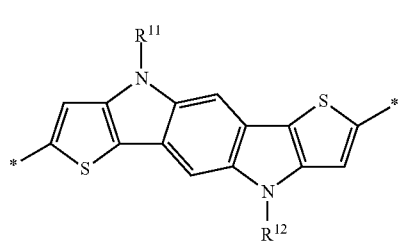
(D61)
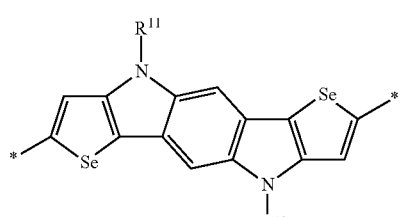
(D62)
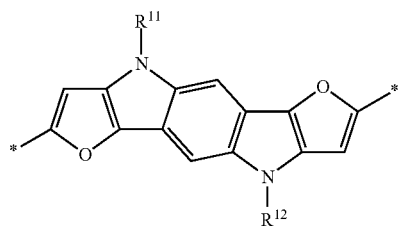
(D63)

(D64) 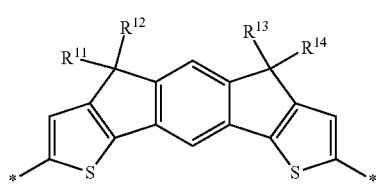
(D65) 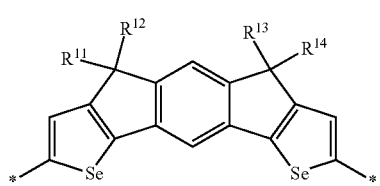
(D66) 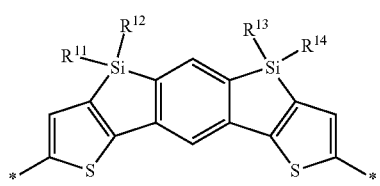
(D67) 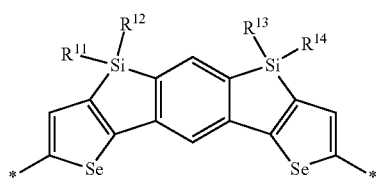
(D68) 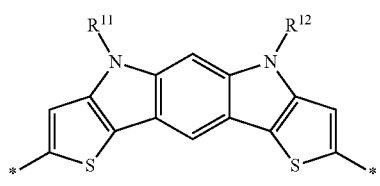
(D69) 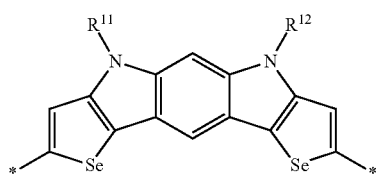
(D70) 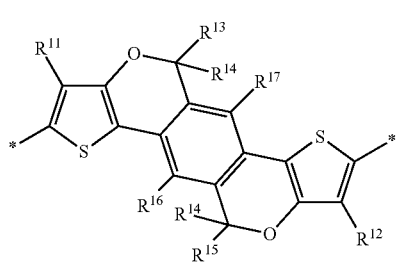
(D71) 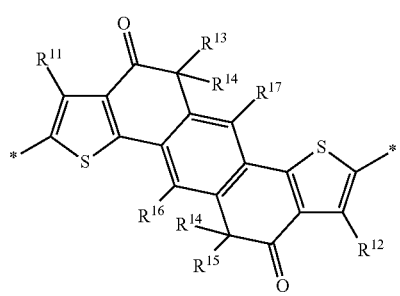
(D72) 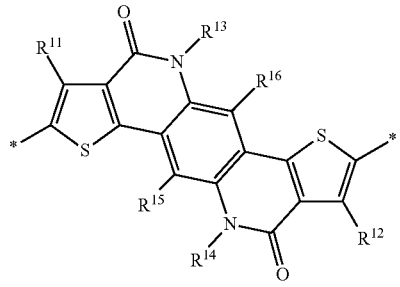
(D73) 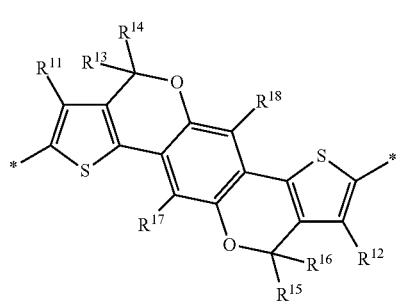
(D74) 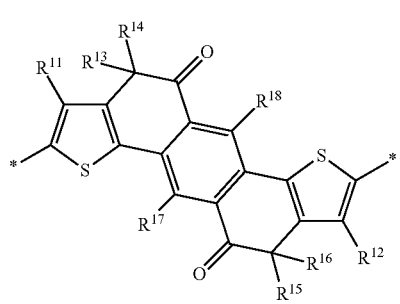
(D75) 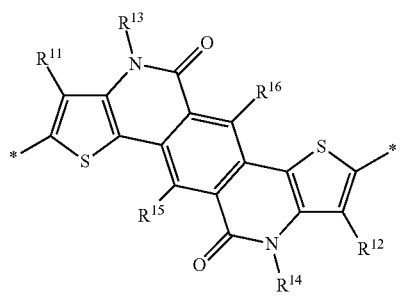

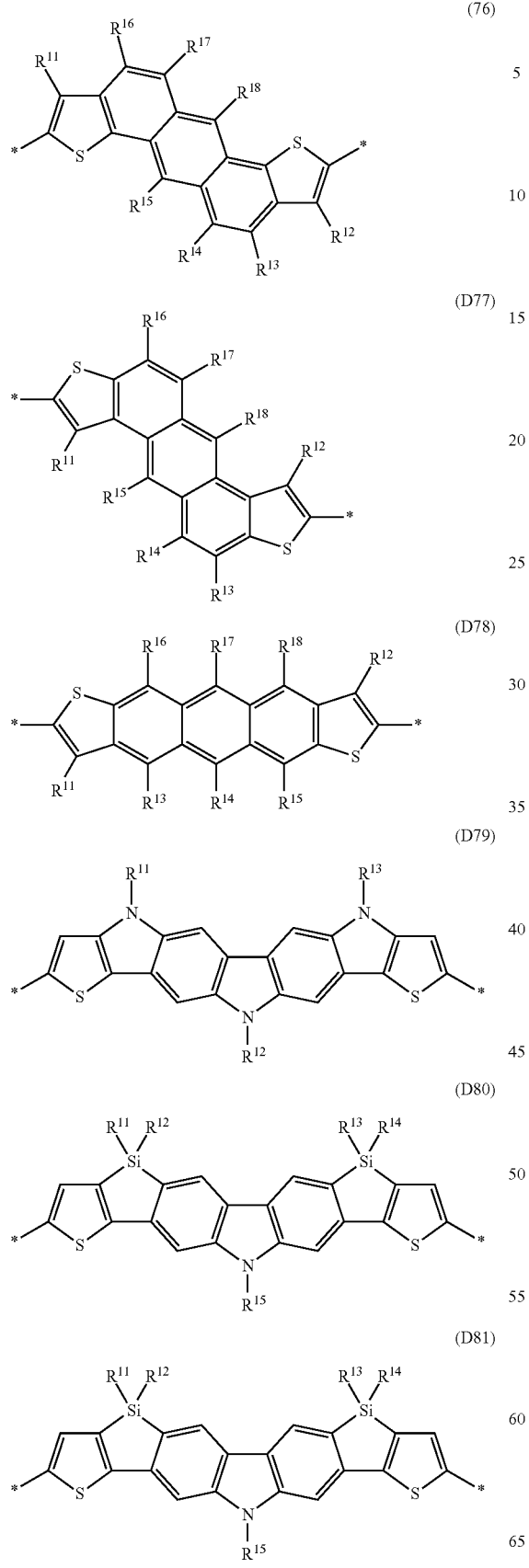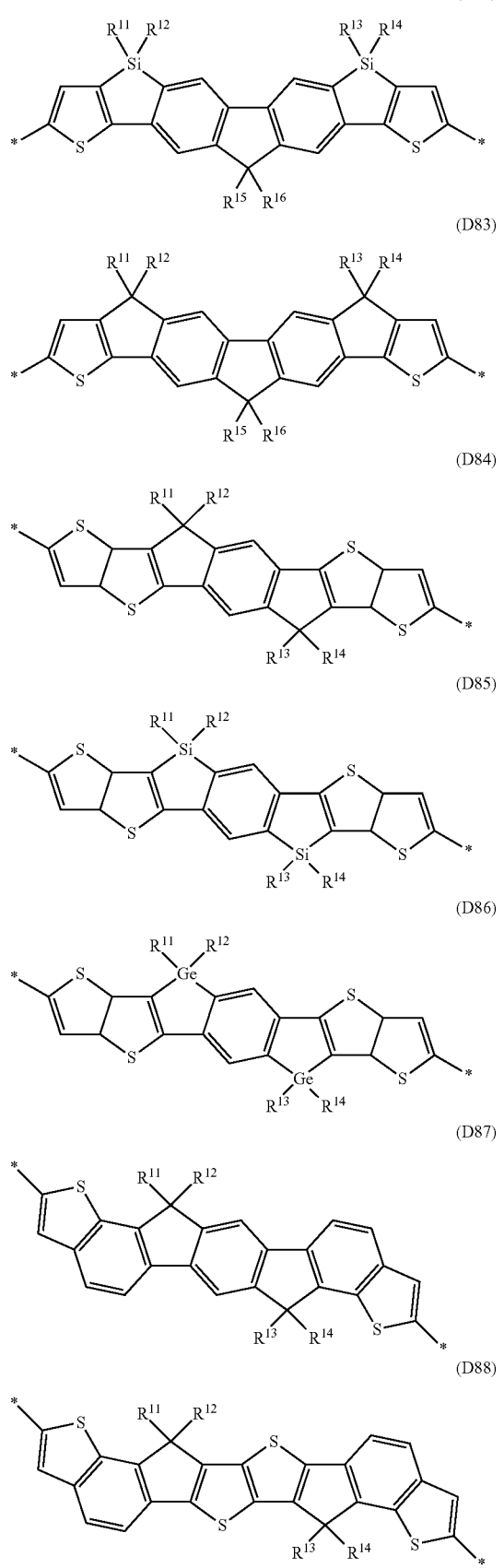

-continued
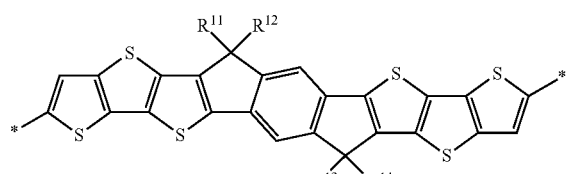 (D89)
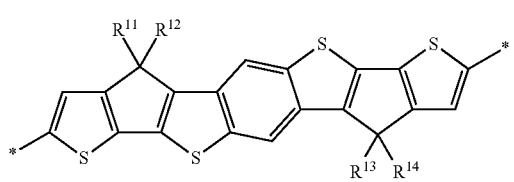 (D90)
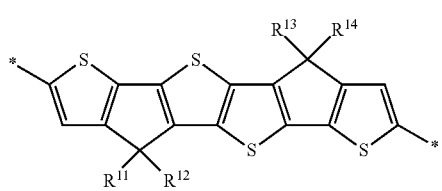 (D91)
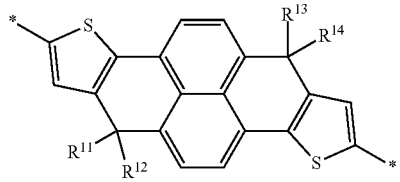 (D92)
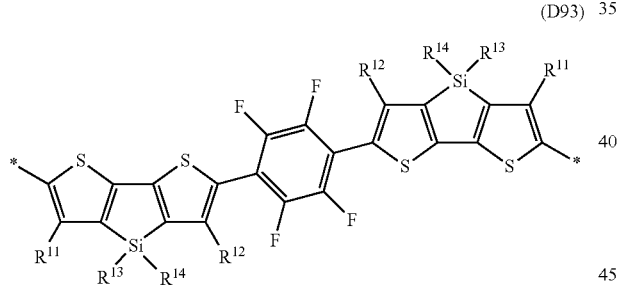 (D93)
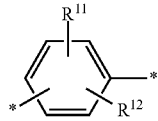 (D94)
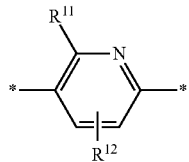 (D95)
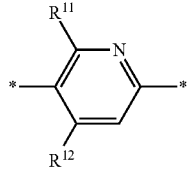 (D96)
-continued
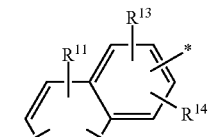 (D97)
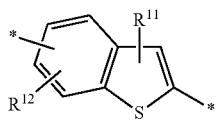 (D98)
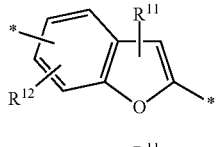 (D99)
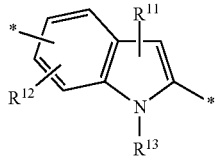 (D100)
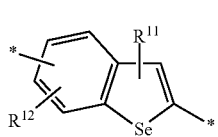 (D101)
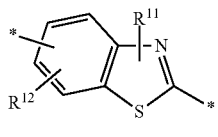 (D102)
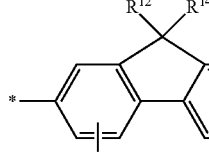 (D103)
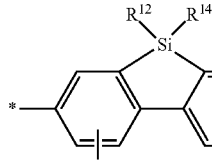 (D104)
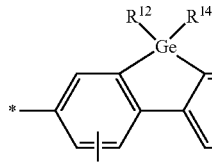 (D105)
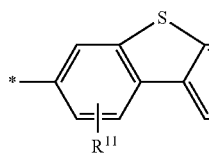 (D106)

-continued
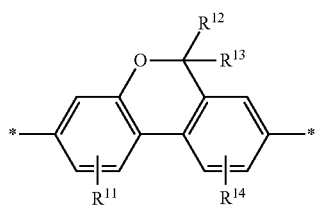
(D107)
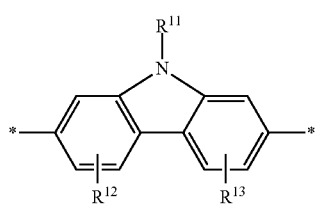
(D108)
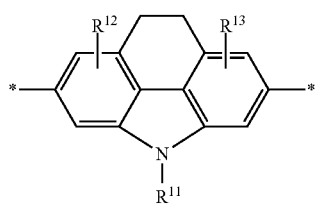
(D109)
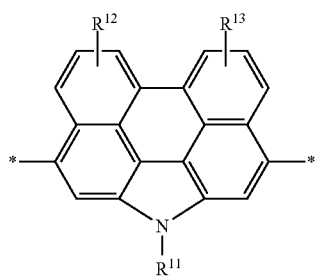
(D110)
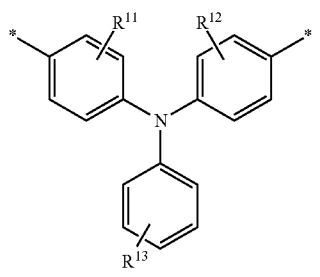
(D111)
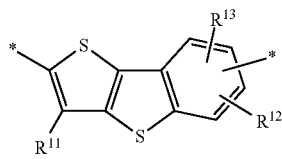
(D112)
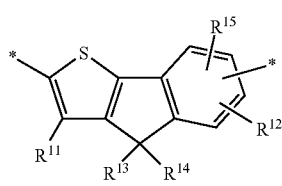
(D113)
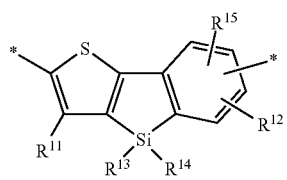
(D114)
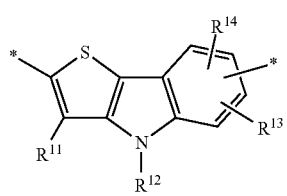
(D115)
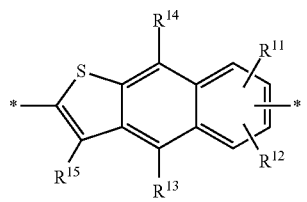
(D116)
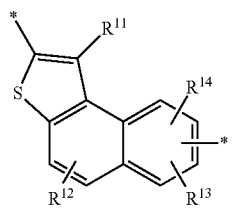
(D117)
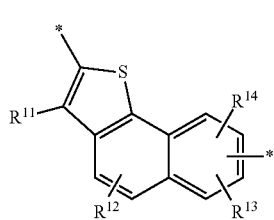
(D118)
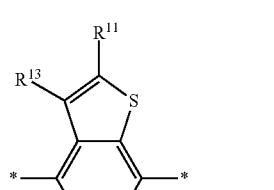
(D119)

-continued
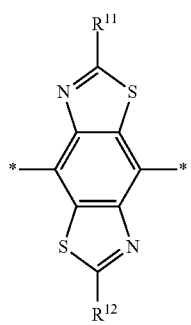
(D120)
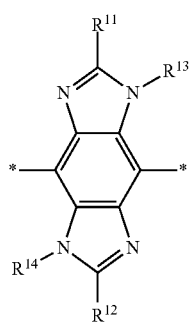
(D121)
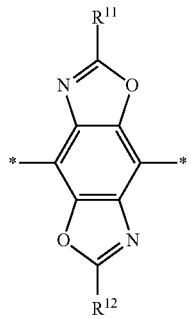
(D122)
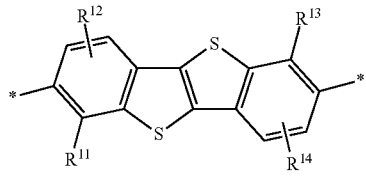
(D123)
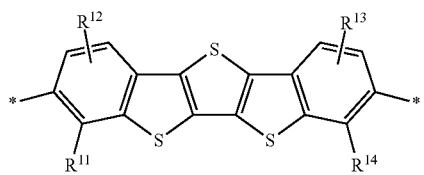
(D124)
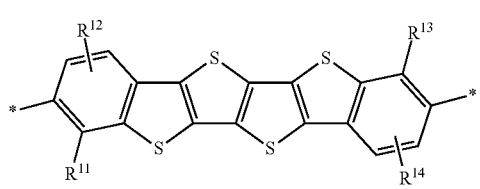
(D125)
-continued
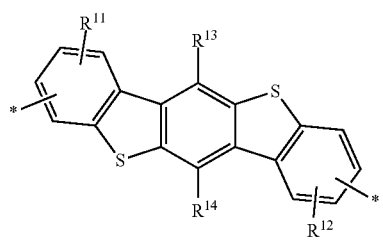
(D126)
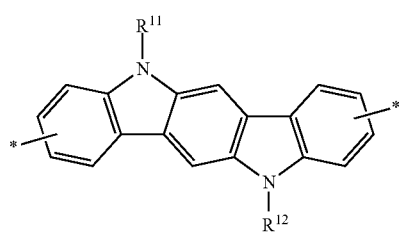
(D127)
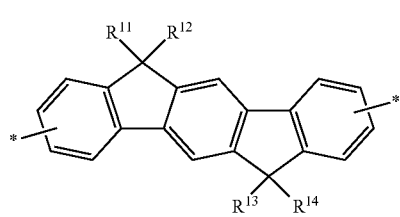
(D128)
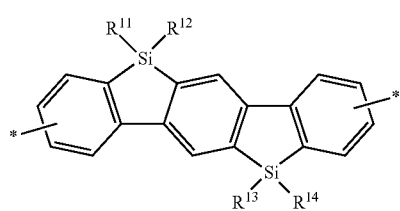
(D129)
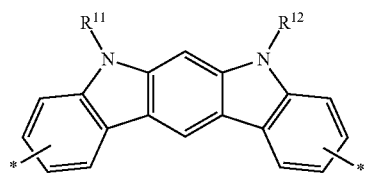
(D130)
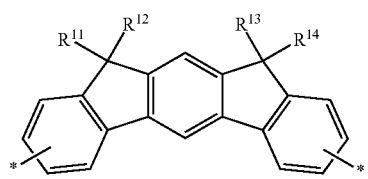
(D131)
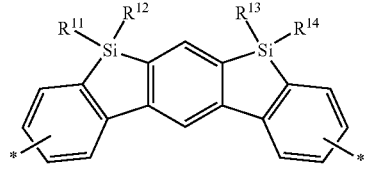
(D132)

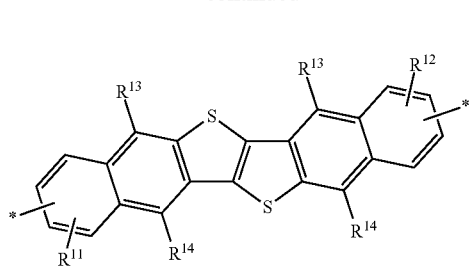 (D133)
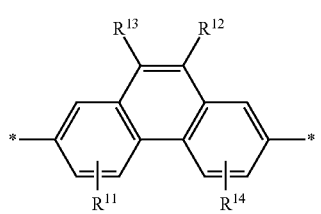 (D134)
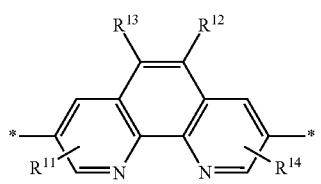 (D135)
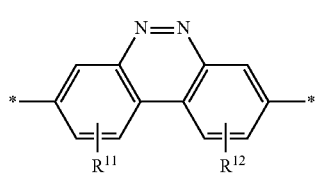 (D136)
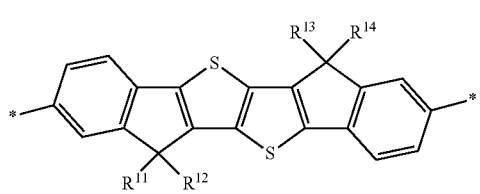 (D137)
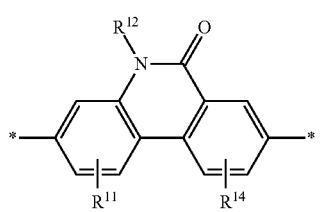 (D138)
wherein $R^{11}$, $R^{12}$, $R^{13}$, $R^{14}$, $R^{15}$, $R^{16}$, $R^{17}$ and $R^{18}$ independently of each other denote H or have one of the meanings of $R^P$ as defined above and below.
In the repeating units and polymers of formulae PIIa, PIIb, PIII, PIV, PIVa-PIVk and PV, preferably Ac, $Ar^1$, $Ar^2$ and $Ar^3$ are selected from the group consisting of the following formulae
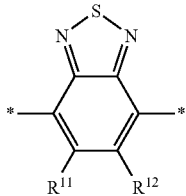 (A1)
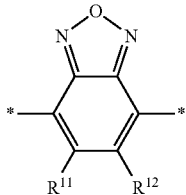 (A2)
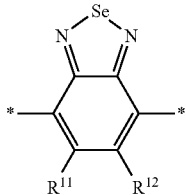 (A3)
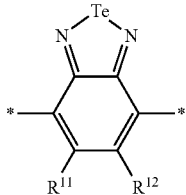 (A4)
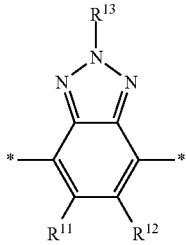 (A5)
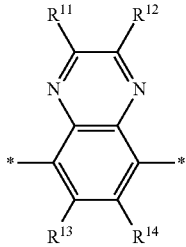 (A6)
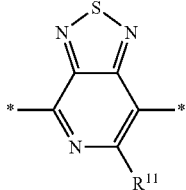 (A7)

-continued
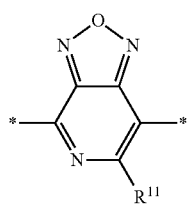 (A8)
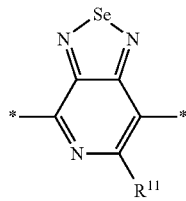 (A9)
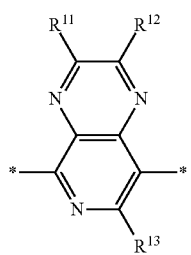 (A10)
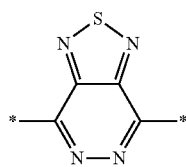 (A11)
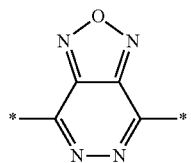 (A12)
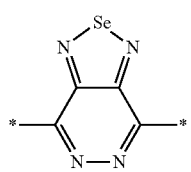 (A13)
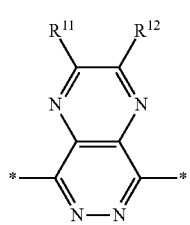 (A14)
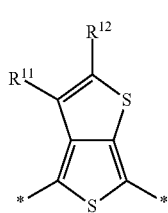 (A15)
-continued
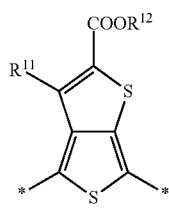 (A16)
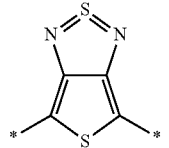 (A17)
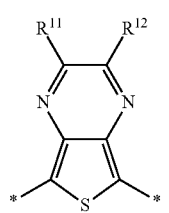 (A18)
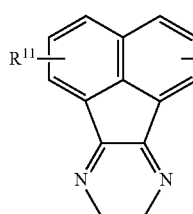 (A19)
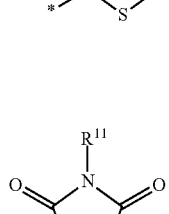 (A20)
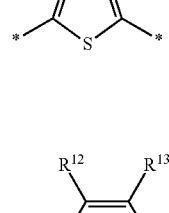 (A21)
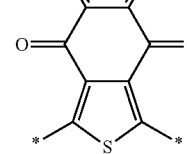

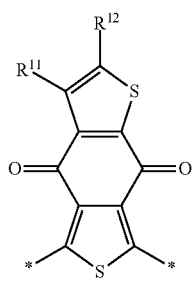
(A22)
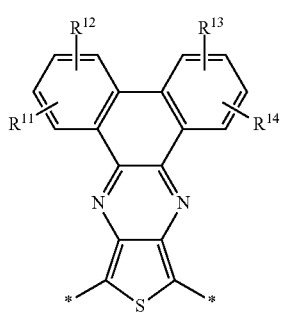
(A23)
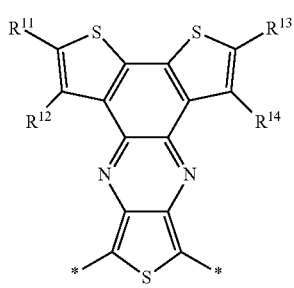
(A24)
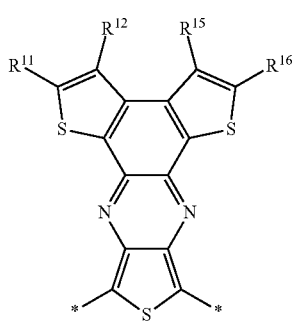
(A25)
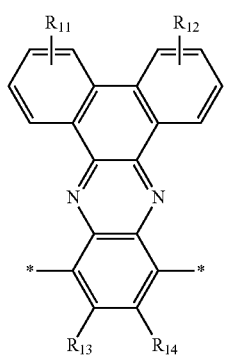
(A26)
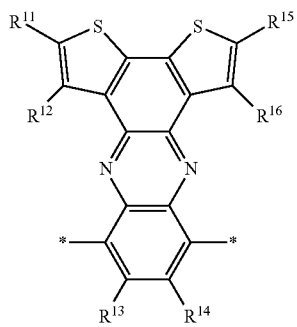
(A27)
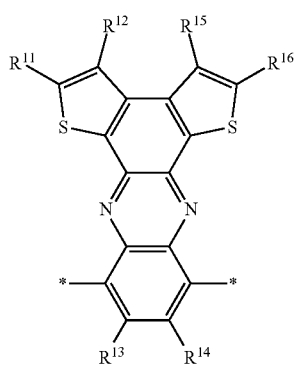
(A28)
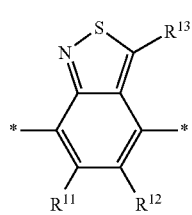
(A29)
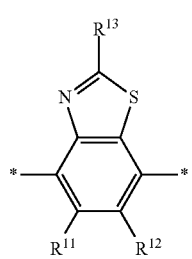
(A30)
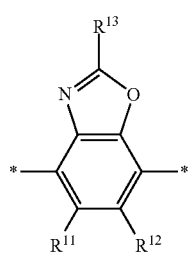
(A31)

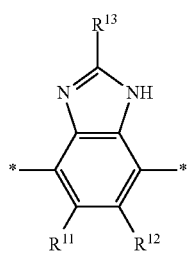 (A32)
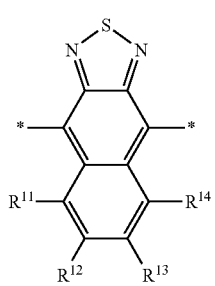 (A33)
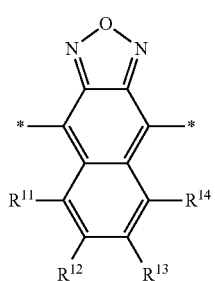 (A34)
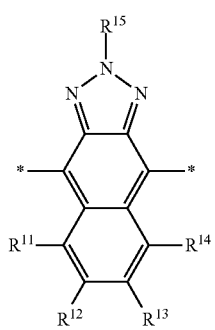 (A35)
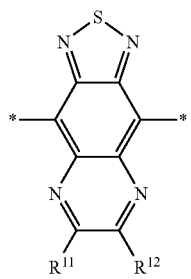 (A36)
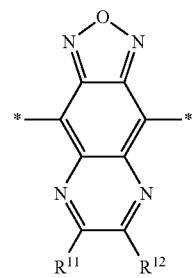 (A37)
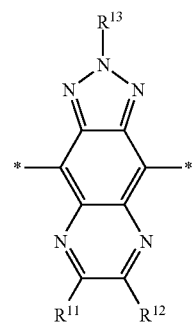 (A38)
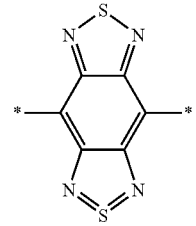 (A39)
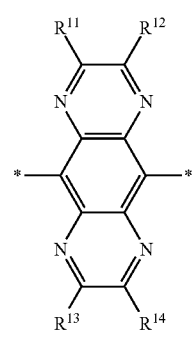 (A40)
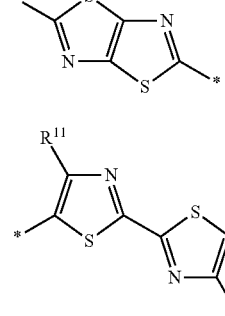 (A41)
(A42)
(A43)

(A44) 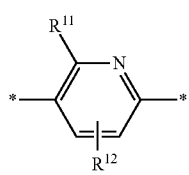
(A45) 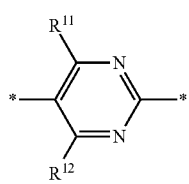
(A46) 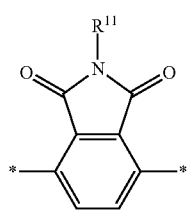
(A47) 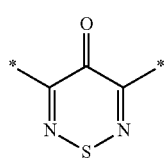
(A48) 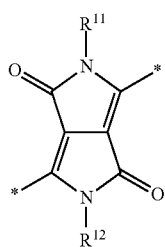
(A49) 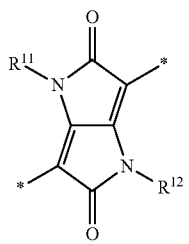
(A50) 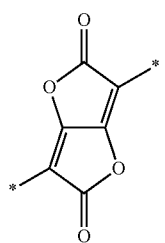
(A51) 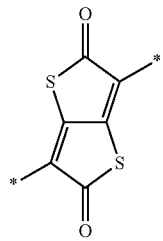
(A52) 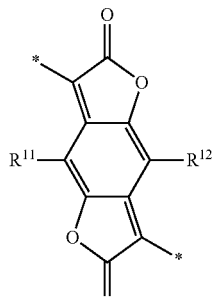
(A53) 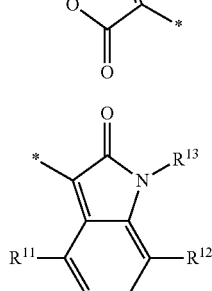
(A54) 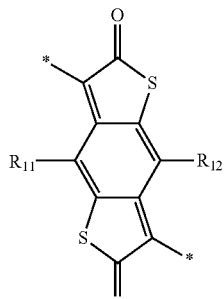
(A55) 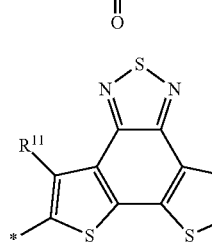
(A56) 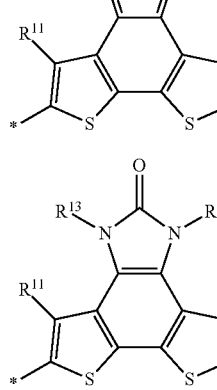

-continued
(A57) 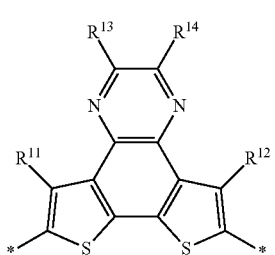
(A58) 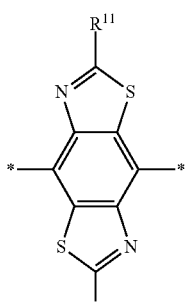
(A59) 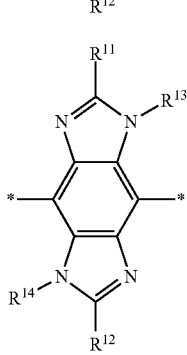
(A60) 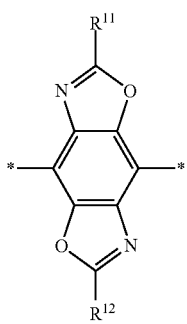
(A61) 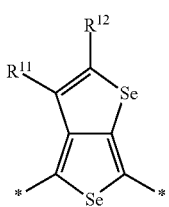
(A62) 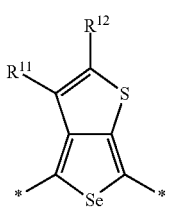
-continued
(A63) 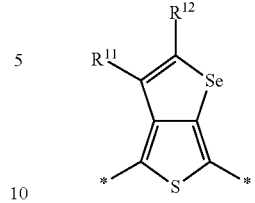
(A64) 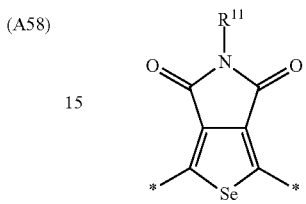
(A65) 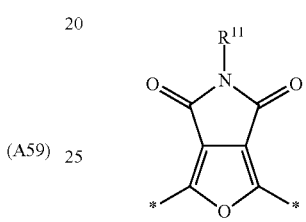
(A66) 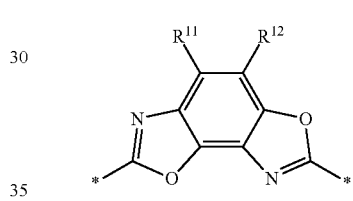
(A67) 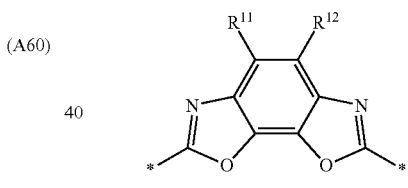
(A68) 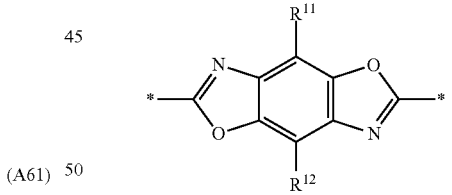
(A69) 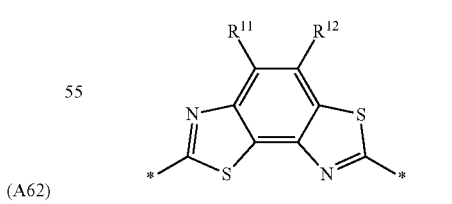
(A70) 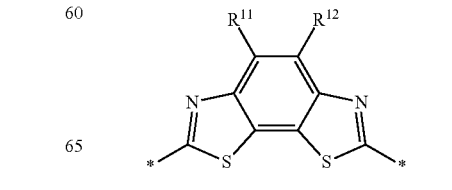

-continued
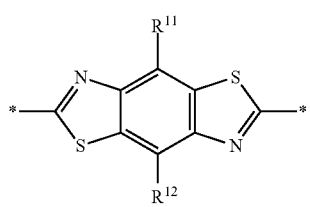
(A71)
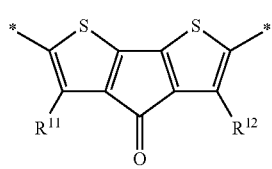
(A72)
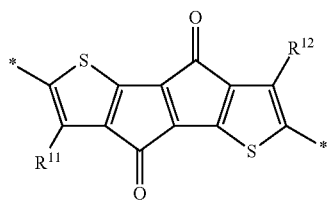
(A73)
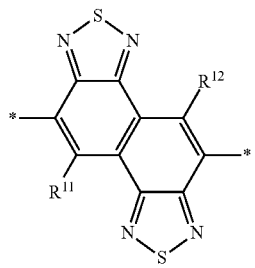
(A74)
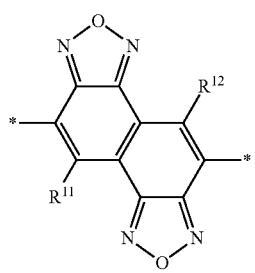
(A75)
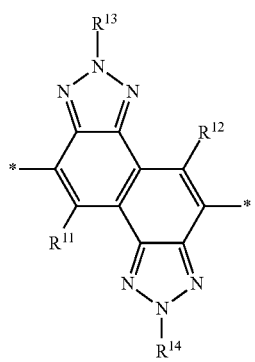
(A76)
-continued
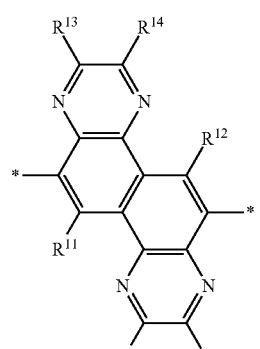
(A77)
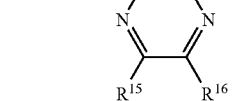
(A78)
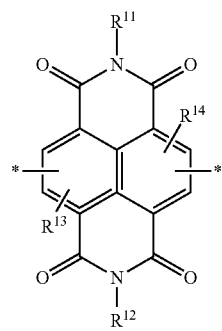
(A79)
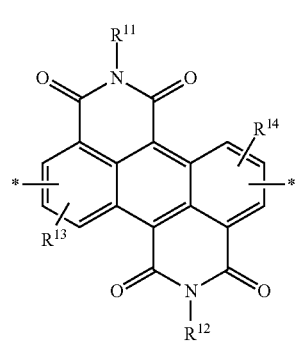
(A80)
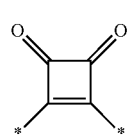
(A81)
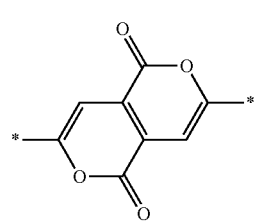
(A82)
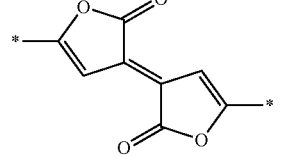

-continued
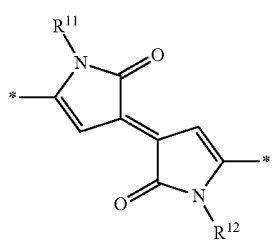
(A83)
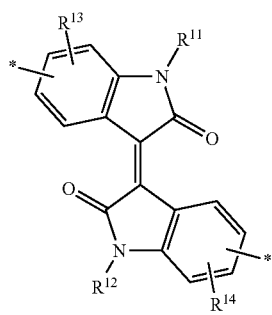
(A84)
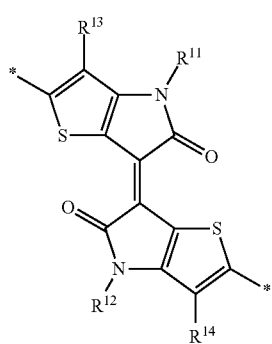
(A85)
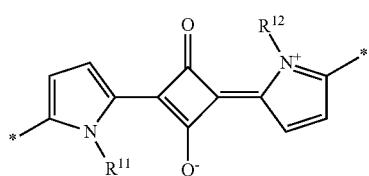
(A86)
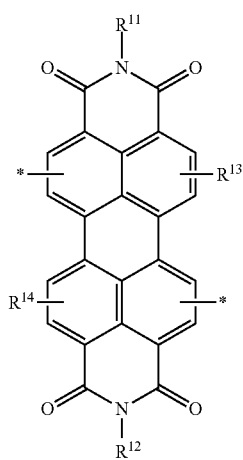
(A87)
-continued
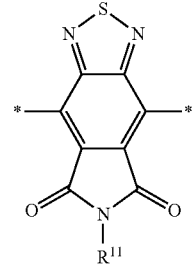
(A88)
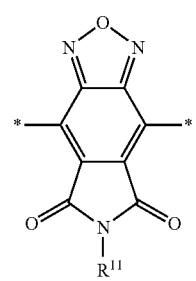
(A89)
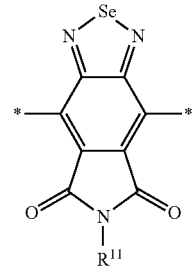
(A90)
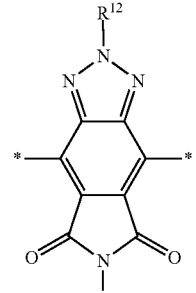
(A91)
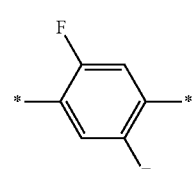
(A92)
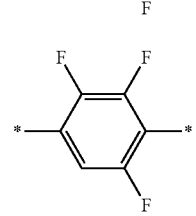
(A93)

-continued

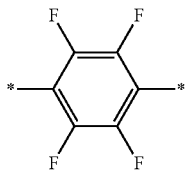
(A94)

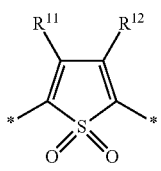
(A95)

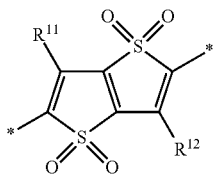
(A96)

wherein $R^{11}$, $R^{12}$, $R^{13}$, $R^{14}$, $R^{15}$ and $R^{16}$ independently of each other denote H or have one of the meanings of $R^P$ as defined above and below.

The polymer can be prepared for example from monomers selected from the following formulae $R^{23}-(Ar^1)_a-D-(Ar^2)_c-R^{24}$     PVIa $R^{23}-D-(Ar^1)_a-D-R^{24}$     PVIb $R^{23}-(Ar^1)_a-Ac-(Ar^2)_c-R^{24}$     PVIc $R^{23}-Ac-(Ar^1)_a-Ac-R^{24}$     PVId $R^{23}-(Ar^1)_a-(Ar^2)_c-R^{24}$     PVIe wherein Ac, D, $Ar^1$, $Ar^2$, a and b have the meanings of formula PIIa and PIIb, or one of the preferred meanings as described above and below, and $R^{23}$ and $R^{24}$ are, preferably independently of each other, selected from the group consisting of H, Cl, Br, I, O-tosylate, O-triflate, O-mesylate, O-nonaflate, $-SiMe_2F$, $-SiMeF_2$, $-O-SO_2Z^1$, $-B(OZ^2)_2$, $-CZ^3=C(Z^3)_2$, $-C\equiv CH$, $-C\equiv CSi(Z^1)_3$, $-ZnX^0$ and $-Sn(Z^4)_3$, wherein $X^0$ is halogen, preferably Cl, Br or I, $Z^{1-4}$ are selected from the group consisting of alkyl and aryl, each being optionally substituted, and two groups $Z^2$ may also together form a cyclic group.

Suitable monomers are for example selected from the following subformulae $R^{23}-Ar^1-D-Ar^2-R^{24}$     PVIa1

$R^{23}-D-R^{24}$     PVIa2

$R^{23}-Ar^1-D-R^{24}$     PVIa3

$R^{23}-D-Ar^2-R^{24}$     PVIa4

$R^{23}-D-Ar^1-D-R^{24}$     PVIb1

$R^{23}-Ar^1-Ac-Ar^2-R^{24}$     PVIc1

$R^{23}-Ac-R^{24}$     PVIc2

$R^{23}-Ar^1-Ac-R^{24}$     PVIc3

$R^{23}-Ac-Ar^2-R^{24}$     PVIc4

$R^{23}-Ac-Ar^1-Ac-R^{24}$     PVId1

$R^{23}-Ar^1-R^{24}$     PVIe1

$R^{23}-Ar^1-Ar^2-R^{24}$     PVIe2 wherein Ac, D, $Ar^1$, $Ar^2$, a, c, $R^{23}$ and $R^{24}$ are as defined in formulae PVIa-PVId.

The polymer can be synthesized according to or in analogy to methods that are known to the skilled person and are described in the literature. Other methods of preparation can be taken from the examples. For example, the polymers can be suitably prepared by aryl-aryl coupling reactions, such as Yamamoto coupling, Suzuki coupling, Stille coupling, Sonogashira coupling, C—H activation coupling, Heck coupling or Buchwald coupling. Suzuki coupling, Stille coupling and Yamamoto coupling are especially preferred. The monomers which are polymerised to form the repeat units of the polymers can be prepared according to methods which are known to the person skilled in the art.

For example the polymer can be prepared by coupling one or more monomers selected from formulae PVIa-PVId and their subformulae in an aryl-aryl coupling reaction, wherein $R^{23}$ and $R^{24}$ are selected from Cl, Br, I, $-B(OZ^2)_2$ and $-Sn(Z^4)_3$.

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in J. Chem. Soc., Chem. Commun., 1977, 683-684. Yamamoto coupling is described in for example in T. Yamamoto et al., Prog. Polym. Sci., 1993, 17, 1153-1205, or WO 2004/022626 A1, and Stille coupling is described for example in Z. Bao et al., J. Am. Chem. Soc., 1995, 117, 12426-12435. For example, when using Yamamoto coupling, monomers having two reactive halide groups are preferably used. When using Suzuki coupling, monomers of formulae PVIa-PVId and their subformulae having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as $Pd(Ph_3P)_4$. Another preferred phosphine ligand is tris(ortho-tolyl)phosphine, i.e. $Pd(o-Tol_3P)_4$. Preferred Pd(II) salts include palladium acetate, i.e. $Pd(OAc)_2$. Alternatively the Pd(0) complex can be prepared by mixing a Pd(0) dibenzylideneacetone complex, for example tris(dibenzyl-ideneacetone)dipalladium(0), bis (dibenzylideneacetone)-palladium(0), or Pd(II) salts e.g. palladium acetate, with a phosphine ligand, for example triphenylphosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

Suzuki and Stille polymerisation may be used to prepare homopolymers as well as statistical, alternating and block random copolymers. Statistical or block copolymers can be prepared for example from the above monomers of formula PVI or its subformulae, wherein one of the reactive groups is halogen and the other reactive group is a boronic acid, boronic acid derivative group or and alkylstannane. The synthesis of statistical, alternating and block copolymers is described in detail for example in WO 03/048225 A2 or WO 2005/014688 A2.

The concentration of the fullerene derivatives of this invention, or of the fullerene composition, in a formulation according to the present invention, including solvents, is preferably 0.1 to 10% by weight, more preferably 0.5 to 5% by weight. The concentration of the fullerene derivatives of this invention in a composition comprising a fullerene derivative and a polymer according to the present invention (i.e. excluding solvents), is preferably from 10 to 90% by weight, very preferably from 33% to 80% by weight.

Another aspect of the present invention relates to a formulation comprising one or more fullerene derivatives of this invention or a fullerene composition as described above, and further comprising one or more solvents, preferably selected from organic solvents.

Such a formulation is preferably used as a carrier for the preparation of a semiconducting layer of an OE device, like an OPV or OPD device, wherein the fullerene derivative or fullerene composition is for example used in the photoactive layer.

Optionally, the formulation further comprises one or more binders to adjust the rheological properties, as described for example in WO 2005/055248 A1.

The formulations according to the present invention preferably form a solution.

The solubility of the inventive fullerene compounds can be enhanced substantially compared to the solubility of a standard compound that is not inventive and used as a standard (see working examples below where o-QDM-$C_{60}$ was used as a standard in o-dichlorobenzene). For example, the solubility of the inventive compound can be at least 2×, 3×, 4×, 5×, 10×, 15×, 20×, or 25× that of the standard. The solubility in a solvent, such as an organic solvent such as, for example, o-dichlorobenze, can be, for example, at least 10 mg/cm$^3$, or at least 20 mg/cm$^3$, or at least 30 mg/cm$^3$, or at least 40 mg/cm$^3$, or at least 50 mg/cm$^3$, or at least 80 mg/cm$^3$, or at least 100 mg/cm$^3$, or at least 150 mg/cm$^3$. There is no particular upper limit on the solubility but the solubility can be, for example, less than 1,000 mg/cm$^3$, or less than 500 mg/cm$^3$, or less than 250 mg/cm$^3$. A test to measure solubility is provided in the working examples. The test temperature can be for example room temperature or ambient temperature such as, for example, about 22° C. Other solvents and fullerene compounds can be used in the exemplified test.

The invention additionally provides an electronic device comprising a fullerene derivative of this invention or fullerene composition, or a semiconducting layer comprising it, as described above and below.

Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular bulk heterojunction (BHJ) OPV devices and OPD devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices, preferably a fullerene composition is used that contains a p-type (electron donor) semiconductor and an n-type (electron acceptor) semiconductor. The p-type semiconductor is for example a conjugated polymer having repeating units of formulae PIIa, PIIb or PIII, or a polymer of formula PIV, PV or their subformulae, as shown above. The n-type semiconductor is a fullerene derivative of this invention, or a mixture of two or more fullerenes, at least one of which is a fullerene derivative of this invention.

Further preferably the OPV or OPD device comprises, between the active layer and the first or second electrode, one or more additional buffer layers acting as hole transporting layer and/or electron blocking layer, which comprise a material such as a metal oxide, like for example, ZTO, $MoO_x$, $NiO_x$, a conjugated polymer electrolyte, like for example PEDOT:PSS, a conjugated polymer, like for example polytriarylamine (PTAA), an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively acting as hole blocking layer and/or electron transporting layer, which comprise a material such as a metal oxide, like for example, $ZnO_x$, $TiO_x$, a salt, like for example LiF, NaF, CsF, a conjugated polymer electrolyte, like for example poly[3-(6-tri-methylammoniumhexyl)thiophene], poly(9,9-bis(2-ethylhexyl)-fluorene]-b-poly[3-(6-trimethylammoniumhexyl)thiophene], or poly[(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a fullerene composition comprising a fullerene derivative and a polymer according to the present invention, the ratio polymer:fullerene derivative is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in OE devices, like BHJ OPV devices, a fullerene derivative, fullerene composition or formulation according to the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

When preparing a suitable solution or formulation containing a composition with a fullerene derivative (as n-type component) and a polymer (as p-type component) according to the present invention, a suitable solvent should be selected so as to ensure full dissolution of both the p-type and the n-type component, and to take into account the boundary conditions (for example rheological properties) introduced by the chosen printing method.

Organic solvents are generally used for this purpose. Typical solvents can be aromatic solvents, halogenated solvents or chlorinated solvents, including chlorinated aromatic solvents. Preferred solvents are aliphatic hydrocarbons, chlorinated hydrocarbons, aromatic hydrocarbons, ketones, ethers and mixtures thereof. Examples include, but are not limited to 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chloro-benzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoromethylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethyl-anisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, 2-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chlorobenzene, o-dichlorobenzene, 1,2,4-dichlorobenzene, 2-chlorofluorobenzene, 1,8-diiodooctane, 1,8-octanedithiol, nitrobenzene, 1-chloronaphthalene, p-xylene, m-xylene, o-xylene or mixture of o-, m-, and p-isomers. Solvents with relatively low polarity are generally preferred. Examples of especially preferred solvents include, without limitation, dichloromethane, trichloromethane, chlorobenzene, o-dichlorobenzene, 1,2,4-dichlorobenzene, anisole, 2,5-dimethylanisole, 2,4-dimethylanisole, morpholine, toluene, o-xylene, m-xylene, p-xylene, 1-methylnaphthalene, 1,8-diiodooctane, 1,8-octanedithiol, nitrobenzene, tetraline, decaline, indane, methyl benzoate, ethyl benzoate, mesitylene and/or mixtures thereof.

The OPV device can be of any OPV device type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode or a conducting grid
  an optional conducting polymer layer or hole transport layer, preferably comprising an organic polymer or polymer blend, for example of PEDOT:PSS (poly(3,4-ethylenedioxythiophene):poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-naphthyl-phenyl)-1,1'biphenyl-4,4'-diamine),
  a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties and/or hole-blocking properties, for example comprising LiF or PFN,
  a low work function electrode, preferably comprising a metal like for example aluminum, serving as cathode,
wherein at least one of the electrodes, preferably the anode, is at least partially transparent to visible light, and
wherein the n-type semiconductor is a fullerene derivative of this invention.

A second preferred OPV device according to the invention is an inverted OPV device and comprises the following layers (in the sequence from bottom to top):
  optionally a substrate,
  a high work function metal or metal oxide electrode, comprising for example ITO, serving as cathode, or a conducting grid
  a layer having hole blocking properties and/or an electron-selective contact, preferably comprising a metal oxide like $TiO_x$ or $ZnO_x$, and/or an organic layer or a polyamine like PEI:DEG or PEIE.
  a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic small-molecule and/or polymer and/or polymer blend, for example of PEDOT:PSS or TBD or NBD,
  an electrode comprising a high work function metal like for example silver, serving as anode,
wherein at least one of the electrodes, preferably the cathode, is at least partially transparent to visible light, and
wherein the n-type semiconductor is a fullerene derivative of this invention.

In the OPV devices of the present invention the p-type and n-type semiconductor materials are preferably selected from the materials, like the polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morpohology and consequently OPV device performance.

Another method to optimize device performance is to prepare formulations for the fabrication of OPV(BHJ) devices that may include additives with variable boiling points to promote phase separation in the right way. 1,8-octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.,* 2010, 132, 7595-7597.

As further illustrated in the non-limiting working examples, photovoltaic devices can be prepared which have a power conversion efficiency (PCE) of, for example, at least 2.5%, or at least 3.0%, or at least 4.0%, or at least 5.0%. While there is no particular upper limit on the PCE, the PCE can be, for example, less than 20%, or less than 15%, or less than 10%.

The fullerene derivatives, fullerene compositions and semiconducting layers of the present invention are also suitable for use as n-type semiconductor in other OE devices or device components, for example in the semiconducting channel of an OFET device, or in the buffer layer, electron transport layer (ETL) or hole blocking layer (HBL) of an OLED or OPV device.

Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a fullerene derivative of this invention, a fullerene composition or an organic semiconducting layer according to the present invention as n-type semiconductor. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
wherein the semiconductor layer comprises a fullerene derivative of this invention or a fullerene composition as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the fullerene derivatives, fullerene compositions, and semiconducting layers according to the invention can be used in OLEDs, for example in the buffer layer, ETL or HBL of an OLED. The OLED device can be used for example as the active display layer in a flat panel display device, or as the backlight of a flat panel display like for example a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer.

The fullerene derivatives, fullerene composition or semiconducting layer according to the present invention may be employed in one or more of the ETL, HBL or buffer layer, especially their water-soluble derivatives (for example with polar or ionic side groups) or ionically doped forms. The processing of such layers, comprising a semiconductor material of the present invention, for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128, O'Malley et al, *Adv. Energy Mater.* 2012, 2, 82-86 and the literature cited therein.

According to another use, the fullerene derivatives, fullerene compositions, and materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of a fullerene derivative according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and LnCl₃ (wherein Ln is a lanthanoid), anions (e.g., Cl⁻, Br⁻, I⁻, I₃⁻, HSO₄⁻, SO₄²⁻, NO₃⁻, ClO₄⁻, BF₄⁻, PF₆⁻, AsF₆⁻, SbF₆⁻, FeCl₄⁻, Fe(CN)₆³⁻, and anions of various sulfonic acids, such as aryl-SO₃⁻). When holes are used as carriers, examples of dopants are cations (e.g., H⁺, Li⁺, Na⁺, K⁺, Rb⁺ and Cs⁺), alkali metals (e.g., Li, Na, K, Rb, and Cs), alkaline-earth metals (e.g., Ca, Sr, and Ba), O₂, XeOF₄, (NO₂⁺) (SbF₆⁻), (NO₂⁺) (SbCl₆⁻), (NO₂⁺) (BF₄⁻), AgClO₄, H₂IrCl₆, La(NO₃)₃. 6 H₂O, FSO₂OOSO₂F, Eu, acetylcholine, R₄N⁺, (R is an alkyl group), R₄P⁺ (R is an alkyl group), R₆A_S⁺ (R is an alkyl group), and R₃S⁺ (R is an alkyl group).

The conducting form of a fullerene derivative of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

According to another use, the fullerene derivatives and fullerene compositions according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The fullerene derivatives, fullerene compositions, and materials according to the present invention may also be combined with photoisomerisable compounds and/or chromophores for use in or as photoalignment layers, as described in US 2003/0021913 A1.

According to another use the fullerene derivatives, fullerene compositions, and materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in ° C. The values of the dielectric constant ∈ ("permittivity") refer to values taken at 20° C. and 1,000 Hz.

The invention will now be described in more detail by reference to the following examples, which are illustrative only and do not limit the scope of the invention.

A) COMPOUND EXAMPLES

Example 1

Example 1.1

1,2-dihexylbenzene (1.2)

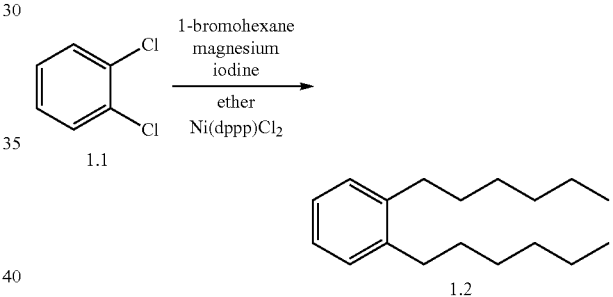

An oil bath was raised to 40° C. To a clean dry 250 mL, 3-necked round bottom flask with stir bar was added 2.48 g (102.0 mmol, 24.305 g/mol, 2.5 eq) of magnesium. The flask was fitted with a condenser, capped and purged three times with nitrogen and vacuum. Anhydrous ethyl ether (100 mL) was added by syringe, and the mixture was stirred and brought to reflux. A trace amount of iodine was added under nitrogen overpressure (reaction became colored and then clear once again). To this mixture was added 14.32 mL (102.0 mmol, 165.07 g/mol, 2.5 eq, 1.176 g/mL) of 1-bromohexane over 1 hour dropwise using a syringe and syringe pump. During the addition, the refluxing became more vigorous and was managed by adjusting the syringe pump speed. The mixture was stirred at reflux for an additional 30 minutes after the addition was complete and then the reaction was allowed to cool. To a second clean dry 500 mL, 3-neck round bottom flask was added a stir bar and 110.6 mg (0.204 mmol, 0.005 eq, 542.04 g/mol) of [1,3-bis(diphenylphosphino)propane]dichloro-nickel(II) catalyst. This second flask was also fitted with a condenser and purged three times with argon and vacuum. Anhydrous ethyl ether (50 mL) and 4.6 mL (40.8 mmol, 147.01 g/mol, 1 eq, 1.306 g/mL) of 1,2-dichlorobenzene (1.1) were both added by syringe and this second mixture was stirred and brought to reflux. The Grignard reagent prepared above was added dropwise using a syringe and syringe pump over 1 hour. Precipitation was observed to begin and then cease during the addition of the unfiltered Grignard. After the addition, additional portions of the nickel catalyst were added under nitrogen overpressure to restart and drive the reaction to completion. Including the original 0.005 eq, a final total of 0.035 eq of the Nickel catalyst was added. Care was taken to control the rate of refluxing. The reaction was removed from the hot bath during catalyst additions. A large quantity of salt was observed to crash out by the time the reaction was nearing completion and stirring speed was adjusted to account for the extra viscosity. The reaction was then allowed to stir at reflux for an additional two nights. After cooling, the reaction was poured into an ice bath and 10% HCl was added cautiously to quench. The mixture was transferred to a separatory funnel, the ether layer was separated from the water layer, the water layer was washed twice with ether, and the ether portions were combined. The ether portions were then washed with water, saturated sodium bicarbonate (Caution! Gas evolution!), and brine, dried with magnesium sulfate, filtered, and the solvent was removed by rotary evaporation. Chromatography on silica in hexanes gave 8 g (79.5% yield) of product (1.2) as a clear oil after rigorous removal of solvent. The final product contained small amounts of hexylbenzene and 1-chloro-2-hexylbenzene by GC-MS. $^1$H NMR (500 MHz, CDCl$_3$ (set to 7.26 ppm)) δ 7.124 (m, 4H), 2.596 (t, J=8.0 Hz, 4H), 1.571 (m, 4H), 1.385 (m, 4H), 1.323 (m, 8H), 0.897 (t, 6H).

Example 1.2

1,2-bis(1-bromohexyl)benzene (1.3)

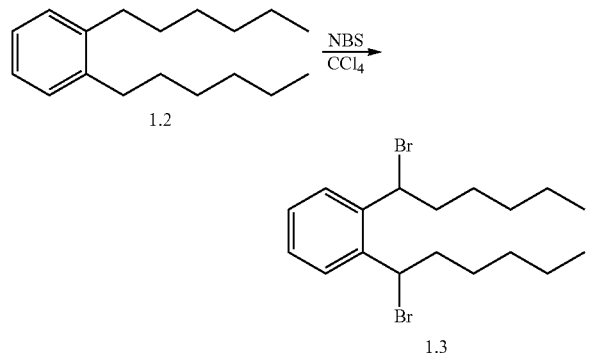

An oil bath was raised to 80° C. To a clean dry 250 mL round bottom flask was added a stir bar, 3.03 g (17.04 mmol, 177.98 g/mol, 2.1 eq) of N-bromosuccinimide, 2 g (8.12 mmol, 246.43 g/mol, 1 eq) of the starting material (1.2) by weight using a dropper, and 12.6 mg of benzoyl peroxide. The flask was fitted with a condenser, then capped and purged three times with nitrogen and vacuum. Anhydrous carbon tetrachloride (50 mL) was added by syringe and the reaction was dropped into the oil bath at 80° C. allowed to stir at reflux overnight. Succinamide is observed to float, indicating that the reaction was complete. The carbon tetrachloride was rotary evaporated, hexane was added, the mixture was sonicated, and the succinamide was removed by filtration. The hexane was then removed by rotary evaporation to give 2.9 g (88% yield) of desired product (1.3) as an oil and possible mixture of isomers. This material was used directly in the next reaction without further purification or other manipulation. It is important to note that this species has been observed to decompose rapidly on silica gel.

Example 1.3

Fullerene 1

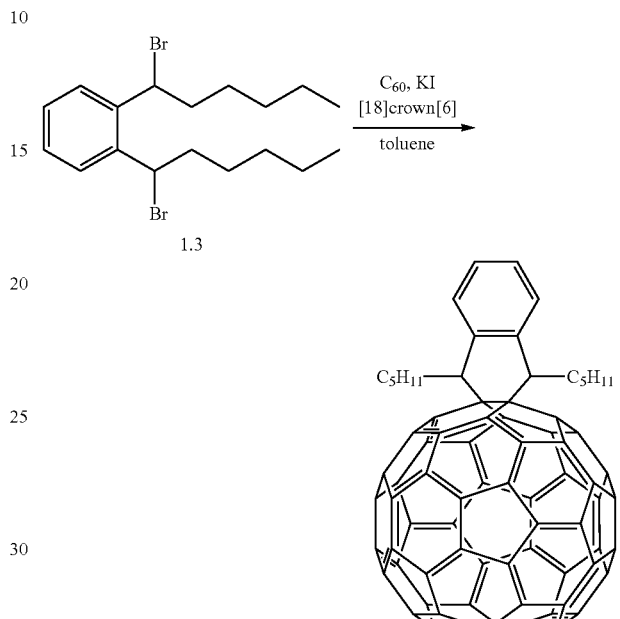

Fullerene 1

An oil bath was brought to 130° C. To a clean dry 500 mL 3-necked round bottom flask containing a stir bar was added 1.334 g (1.85 mmol, 2 eq, 720.64 g/mol) of C$_{60}$ fullerene, 0.6635 g (3.997 mmol, 4.32 eq, 166.00 g/mol) of potassium iodide, and 3.977 g (15.05 mmol, 16.26 eq, 264.32 g/mol) of [18]crown[6]. The round bottom was fitted with a condenser, sealed and purged three times with nitrogen and vacuum. Anhydrous toluene (~330 mL) was added by canula and the mixture was allowed to reach reflux. 374 mg (0.925 mmol, 1 eq, 404.22 g/mol, 1.312 g/mL) of the dibromide (1.3) was then added by syringe in anhydrous toluene and the reaction was refluxed and stirred in the dark overnight. After cooling, the reaction mixture was washed with 5% sodium hydroxide solution and water (350 mL), dried with magnesium sulfate, filtered, and toluene was removed by rotary evaporation. The crude material was purified using silica gel chromatography with decalin as the eluent, followed by preparative intermediate pressure liquid chromatography using a column with Cosmosil Buckyprep material as the stationary phase (from Nacalai Tesque; pyrenylpropyl group bonded silica) and toluene as the mobile phase. Fractions containing pure product were combined and solvent removed using rotary evaporation. The sample was left in an oven overnight at 70° C. under reduced pressure to remove residual solvent. The product (Fullerene 1) was isolated (230 mg, 25.8%) as a brown crystalline solid. Purity was confirmed at 99.59% by analytical HPLC using a column with Cosmosil Buckyprep material as the stationary phase (from Nacalai Tesque; pyrenylpropyl group bonded silica) and toluene as the mobile phase. $^1$H NMR (500 MHz, toluene-d$_8$ (methyl set to 2.09 ppm)) δ 7.527 (AA' of AA'BB', 2H), 7.411 (BB' of AA'BB', 2H), aliphatic signals not assigned with certainty.

Example 2

Example 2.1

Fullerene 2

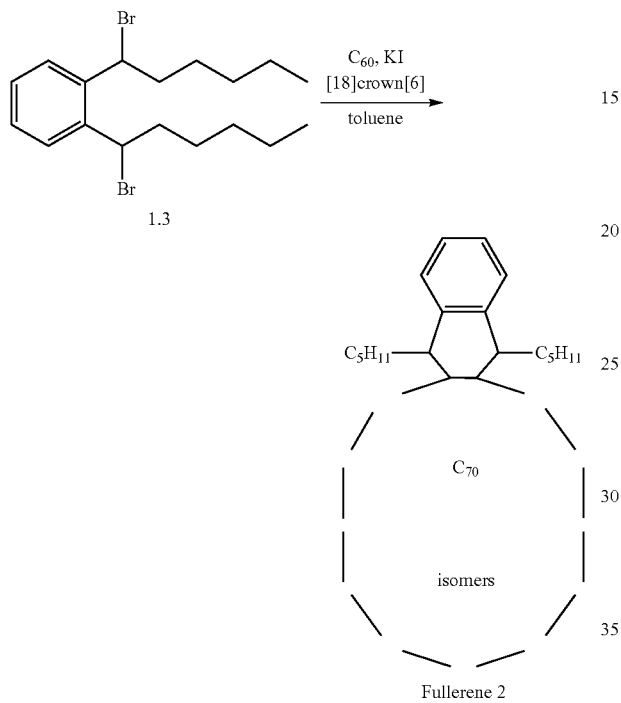

An oil bath was brought to 130° C. To a clean dry 500 mL 3-necked round bottom flask containing a stir bar was added 1 g (1.19 mmol, 1.5 eq, 840.75 g/mol) of $C_{70}$ fullerene, 0.5686 g (3.43 mmol, 4.32 eq, 166.00 g/mol) of potassium iodide, and 3.41 g (12.90 mmol, 16.26 eq, 264.32 g/mol) of [18]crown[6]. The round bottom was fitted with a condenser, sealed and purged three times with nitrogen and vacuum. Anhydrous toluene (~285 mL) was added by canula and the mixture was allowed to reach reflux. 320.5 mg (0.793 mmol, 1 eq, 404.22 g/mol, 1.312 g/mL) of the dibromide (1.3) was then added by syringe in anhydrous toluene and the reaction was refluxed and stirred in the dark overnight. After cooling, the reaction mixture was washed with 5% sodium hydroxide solution and water (350 mL), dried with magnesium sulfate, filtered, and toluene was removed by rotary evaporation. The crude material was purified using silica gel chromatography with decalin as the eluent, followed by preparative intermediate pressure liquid chromatography using a column with Cosmosil Buckyprep material as the stationary phase (from Nacalai Tesque; pyrenylpropyl group bonded silica) and toluene as the mobile phase. Fractions containing pure product were combined and solvent removed using rotary evaporation. The sample was left in an oven overnight at 70° C. under reduced pressure to remove residual solvent. The product (Fullerene 2) was isolated (300.3 mg, 34.9%) as a dark brown crystalline solid. Purity was confirmed at 99.61% for the mixture of isomers by analytical HPLC using a column with Cosmosil Buckyprep material as the stationary phase (from Nacalai Tesque; pyrenylpropyl group bonded silica) and toluene as the mobile phase.

Example 3

Example 3.1

1,2-dipentylbenzene (3.1)

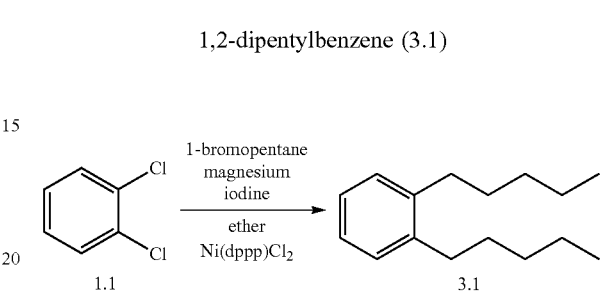

An oil bath is raised to 40° C. To a clean dry 250 cm³, 3-necked round bottom flask with stir bar is added 1.24 g (51.0 mmol, 2.50 eq) of magnesium. The flask is fitted with a condenser, capped and purged three times with nitrogen and vacuum. Anhydrous diethyl ether (50 cm³) is added by syringe, and the mixture is stirred and brought to reflux. A trace amount of iodine is added under nitrogen overpressure. To this mixture is added 6.33 cm³ (51.0 mmol, 2.50 eq) of 1-bromopentane over 1 hour dropwise using a syringe and syringe pump. During the addition, the refluxing became more vigorous and is managed by adjusting the syringe pump speed. The mixture is stirred at reflux for an additional 30 minutes after the addition is complete and then the reaction is allowed to cool. To a second clean dry 250 cm³, 3-neck round bottom flask is added a stir bar and 443 mg (0.816 mmol, 0.0400 eq) of [1,3-bis(diphenylphosphino)-propane]dichloronickel(II). This second flask is also fitted with a condenser and purged three times with nitrogen and vacuum. Anhydrous diethyl ether (25 cm³) and 2.3 cm³ (20.4 mmol) of 1,2-dichlorobenzene (1.1) are both added by syringe and this second mixture is stirred and brought to reflux. The Grignard reagent prepared above is added dropwise without filtering, using a syringe and syringe pump over 1 hour. After the Grignard reagent is added, another 443 mg (0.816 mmol, 0.0400 eq) of [1,3-bis(diphenyl-phosphino)propane]dichloro-nickel(II) is added under nitrogen overpressure. The reaction is then allowed to stir at reflux for three nights. After cooling, the reaction is poured into an ice bath with stirring and 10% hydrochloric acid is added cautiously to quench. The mixture is transferred to a separatory funnel, the diethyl ether layer is separated from the water layer, the water layer is ished twice with ether, and the ether portions are combined. The ether portions are then washed with water, saturated sodium bicarbonate, and brine, dried with magnesium sulfate, filtered, and the solvent is removed by rotary evaporation. Chromatography on silica in hexanes gave 2.15 g (48.2% yield) of the title product as a clear oil after rigorous removal of solvent. ¹H NMR (500

MHz, CDCl$_3$ (set to 7.26 ppm)) δ 7.128 (m, 4H), 2.600 (t, J=8.0 Hz, 4H), 1.582 (m, 4H), 1.4-1.3 (m, 8H), 0.912 (t, 6H).

Example 3.2

1,2-bis(1-bromopentyl)benzene (3.2)

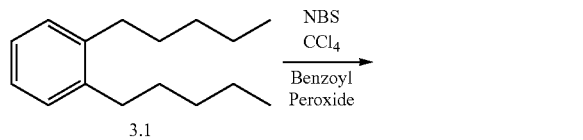

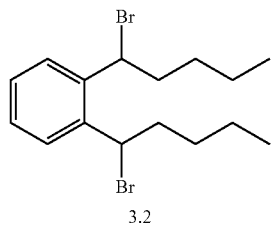

An oil bath is raised to 80° C. To a clean dry 100 cm$^3$ round bottom flask is added a stir bar, 1.20 g (6.73 mmol, 2.10 eq) of N-bromosuccinimide, 0.700 g (3.21 mmol, 1.00 eq) of the starting material (3.1) by weight using a dropper and 5 mg of benzoyl peroxide. The flask is fitted with a condenser, then capped and purged three times with nitrogen and vacuum. Carbon tetrachloride (17.5 cm$^3$) is added by syringe and the reaction is dropped into the oil bath at 80° C. and allowed to stir at reflux overnight. The carbon tetrachloride is removed in vacuo, hexane is added, the mixture is sonicated, and the succinamide removed by filtration. The hexane is then removed in vacuo to give 1.21 g (quantitative) of desired product (3.2) as an oil and possible mixture of isomers. This material was used directly in the next reaction without further purification or other manipulation.

Example 3.3

Fullerene 3

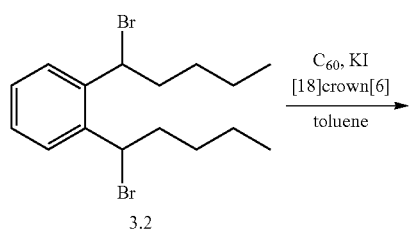

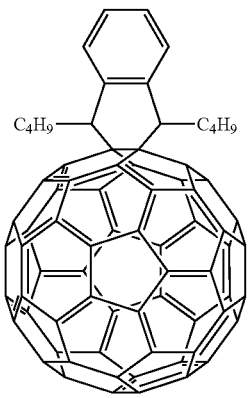

Fullerene 3

An oil bath is brought to 130° C. To a clean dry 2 dm$^3$ round bottom flask containing a stir bar is added ~1.3 dm$^3$ of toluene, 2.88 g (4.00 mmol, 2.00 eq) of C$_{60}$ fullerene, 1.43 g (8.64 mmol, 4.32 eq) of potassium iodide, and 8.60 g (32.5 mmol, 16.3 eq) of [18]crown[6]. The round bottom is fitted with a condenser, sealed and purged three times with nitrogen and vacuum. The mixture is lowered into the oil bath and allowed to reach reflux. 752.4 mg (2.00 mmol, 1 eq, 376.18 g/mol) of 1,2-bis(1-bromopentyl)benzene (3.2) is then added by syringe in ~137 cm$^3$ of toluene. The reaction is refluxed and stirred in the dark overnight. After cooling, the reaction mixture is washed with two times with 250 cm$^3$ of 10% sodium hydroxide solution and with two times with 250 cm$^3$ of water, dried with magnesium sulfate, filtered, and toluene is removed by rotary evaporation. The crude material is purified using silica gel chromatography with decalin as the eluent (twice on the same column) to remove C$_{60}$, followed by preparative intermediate pressure liquid chromatography using a column with Cosmosil Buckyprep material as the stationary phase (from Nacalai Tesque; pyrenylpropyl group bonded silica) and toluene as the mobile phase. Fractions containing pure product are combined and solvent removed using rotary evaporation. The sample is left in an oven overnight at 70° C. under reduced pressure to remove residual solvent. Fullerene 3 is isolated (376 mg, 20%) as a brown crystalline solid.

Example 4

Example 4.1

1,2-diheptylbenzene (4.1)

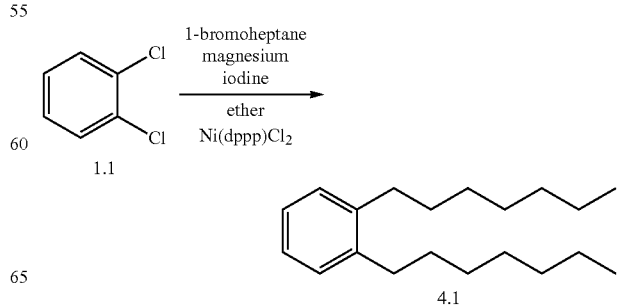

An oil bath is raised to 40° C. To a clean dry 250 cm³, 3-necked round bottom flask with stir bar is added 2.70 g (111 mmol, 2.50 eq) of magnesium. The flask is fitted with a condenser, capped and purged three times with nitrogen and vacuum. Anhydrous diethyl ether (125 cm³) is added by syringe, and the mixture is stirred and brought to reflux. A trace amount of iodine is added under nitrogen overpressure. To this mixture is added 17.5 cm³ (111 mmol, 2.50 eq) of 1-bromoheptane over 1 hour dropwise using a syringe and syringe pump. The mixture is stirred at reflux for an additional 30 minutes after the addition is complete and then the reaction is allowed to cool. To a second clean dry 500 cm³, 3-neck round bottom flask is added a stir bar and 1.20 g (2.21 mmol, 0.0500 eq) of [1,3-bis(diphenylphosphino)propane]dichloronickel(II). This second flask is also fitted with a condenser and purged three times with nitrogen and vacuum. Anhydrous diethyl ether (62.5 cm³) and 1,2-dichlorobenzene (1.1) (5.00 cm³, 44.4 mmol, 1.00 eq) are both added by syringe and this second mixture is stirred and brought to reflux. The Grignard reagent prepared above is added dropwise using a syringe and syringe pump over 45 minutes while concurrently filtering through a wide PTFE filter. After the Grignard is added, another 600 mg (1.11 mmol, 0.0250 eq) of [1,3-bis(diphenylphosphino)propane]dichloronickel(II) is added under nitrogen overpressure. The reaction is allowed to stir at reflux overnight. After cooling, the reaction is poured into an ice bath with stirring and 10% hydrochloric acid (92 cm³, 2.5 eq) is added cautiously to quench. The mixture is transferred to a separatory funnel, the diether layer is separated from the water layer, the water layer is washed twice with diethyl ether, and the organic fractions are combined. The organic fractions are then washed with water, saturated sodium bicarbonate, and brine, dried with magnesium sulfate, filtered, and the solvent is removed in vacuo. Hexane is added and a precipitation is observed. The precipitate is filtered out through a small silica plug which is then rinsed with generous hexane. The solvent filtrate is removed in vacuo to give 9.61 g of a nearly colorless oil. The oil is then subjected to distillation on Kugelrohr for ~30 minutes at 150° C. and high vacuum to give 4.8 g (39.3% yield) of product (4.1) as a clear nearly colorless oil. $^1$H NMR (500 MHz, CDCl$_3$ (set to 7.26 ppm)) δ 7.147 (m, 4H), 2.620 (t, J=8.0 Hz, 4H), 1.55-1.65 (m, 4H), 1.45-1.25 (m, 16H), 0.915 (t, 6H).

Example 4.2

1,2-bis(1-bromoheptyl)benzene (4.2)

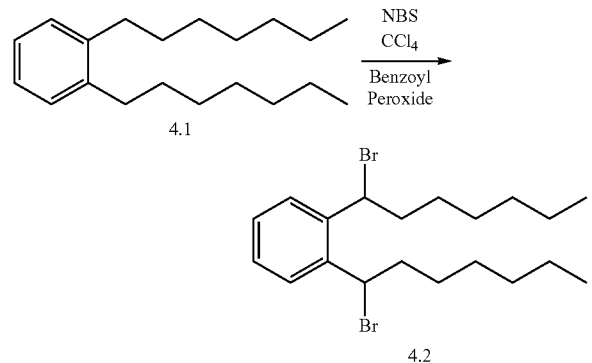

An oil bath is raised to 80° C. To a clean dry 100 cm³ round bottom flask is added a stir bar, 4.28 g (24.1 mmol, 2.20 eq) of N-bromosuccinimide, 3.00 g (10.9 mmol, 1.00 eq) of 1,2-diheptylbenzene (4.1) and 17.1 mg of benzoyl peroxide. The flask is fitted with a condenser, then capped and purged three times with nitrogen and vacuum. Carbon tetrachloride (60 cm³) is added by syringe and the reaction is dropped into the oil bath at 80° C. and allowed to stir at reflux overnight. The carbon tetrachloride is removed in vacuo, hexane is added, the mixture is sonicated, and the succinimide is removed by filtration. The hexane is then removed in vacuo to give 4.75 g (quantitative) of title product (4.2) as an oil and possible mixture of isomers. This material is used directly in the next reaction without further purification or other manipulation.

Example 4.3

Fullerene 4

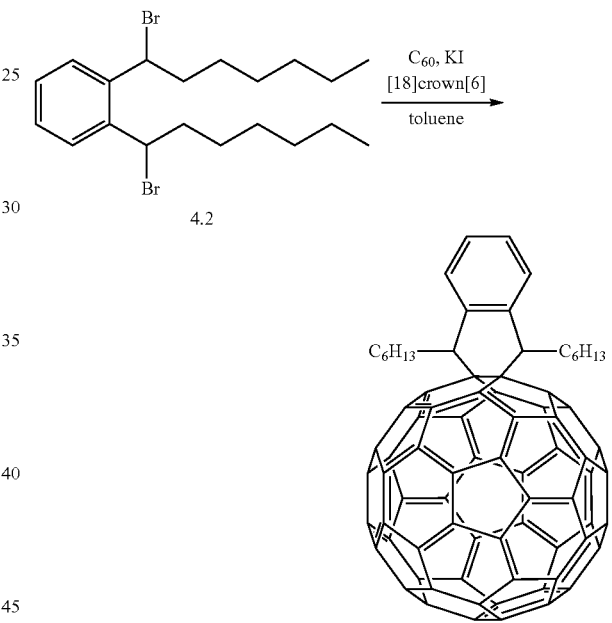

Fullerene 4

An oil bath is brought to 130° C. To a clean dry 2 dm³, two-neck, round bottom flask containing a stir bar is added 11.8 g (16.4 mmol, 1.50 eq) of C$_{60}$ fullerene, 7.84 g (47.2 mmol, 4.32 eq) of potassium iodide, 47.0 g (177.74 mmol, 16.3 eq) of [18]crown[6] and 1.5 dm³ of toluene. The round bottom is fitted with a condenser, sealed and purged three times with nitrogen and vacuum. The mixture is lowered into the oil bath and allowed to reach reflux. 4.73 g (10.9 mmol, 1.00 eq) of the dibromide 1,2-bis(1-bromoheptyl)benzene (4.2) is then added dropwise using a syringe and syringe pump in ~40 cm³ of toluene over 3 hours. The reaction is refluxed and stirred in the dark overnight after lowering the oil bath temperature to 125° C. After cooling, the reaction mixture is washed two times with 840 cm³ of 5% sodium hydroxide solution. After the washings the entire solution is filtered to give 6.44 g of nearly pure, dry C$_{60}$. The filtrate is then washed two times with 840 cm³ of water, dried with magnesium sulfate, filtered, and toluene is removed in vacuo. The crude material is purified using silica gel chromatography with decalin as the eluent to remove $C_{60}$, followed by preparative intermediate pressure liquid chromatography using a column with Cosmosil Buckyprep material as the stationary phase (from Nacalai Tesque; pyrenylpropyl group bonded silica) and toluene as the mobile phase. Fractions containing high purity product are collected and combined. Most of the toluene is removed in vacuo. The bulk of the fullerene adduct precipitated and is filtered off to further improve purity. Samples are left in an oven overnight at 70° C. under reduced pressure to remove residual solvent. Fullerene 4 was isolated in two fractions (968.6 mg and 584.5 mg, 14.3% total yield) as a brown crystalline solid. Purity is confirmed at 99.78% and 99.41% respectively by analytical HPLC using a column with Cosmosil Buckyprep material as the stationary phase (from Nacalai Tesque; pyrenylpropyl group bonded silica) and toluene as the mobile phase.

Example 5

Example 5.1

1,2-dioctylbenzene (5.1)

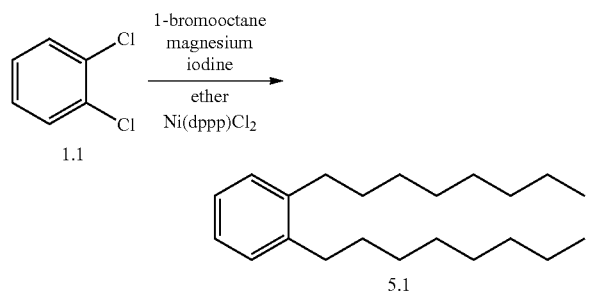

An oil bath is raised to 40° C. To a clean dry 250 cm³, 3-necked round bottom flask with stir bar is added 2.70 g (111 mmol, 2.50 eq) of magnesium. The flask is fitted with a condenser, capped and purged three times with nitrogen and vacuum. Anhydrous diethyl ether (40 cm³) is added by syringe, and the mixture is stirred and brought to reflux. A trace amount of iodine is added under nitrogen overpressure. To this mixture is added 19.2 cm³ (111 mmol, 2.50 eq) of 1-bromooctane over 1 hour dropwise using a syringe and syringe pump. The mixture is stirred at reflux for an additional 30 minutes after the addition is completed and then the reaction is allowed to cool. To a second clean dry 500 cm³, 3-neck round bottom flask is added a stir bar and 1.20 g (2.21 mmol, 0.0500 eq) of [1,3-bis(diphenylphosphino)propane]dichloronickel(II). This second flask is also fitted with a condenser and purged three times with nitrogen and vacuum. Anhydrous diethyl ether (148 cm³) and 1,2-dichlorobenzene (1.1) (5.00 cm³, 44.4 mmol) are both added by syringe and this second mixture is stirred and brought to reflux. The Grignard reagent prepared above is added dropwise using a syringe and syringe pump over 45 minutes while concurrently filtering through a wide PTFE filter. The reaction is allowed to stir at reflux for four days. After cooling, the reaction is poured into an ice bath with stirring and 10% hydrochloric acid (92 cm³, 2.5 eq) is added cautiously to quench. The mixture is transferred to a separatory funnel, the diethyl ether layer is separated from the water layer, the water layer is washed twice with diethyl ether, and the organic fractions are combined. The organic fractions are then washed with water, saturated sodium bicarbonate, and brine, dried with magnesium sulfate, filtered, and the solvent is removed in vacuo. Hexane (250 cm³) is added and a precipitation is observed. The precipitate is filtered out through a small silica plug which is then rinsed with generous hexane. The solvent filtrate is removed in vacuo and the resulting oil is then subjected to distillation on Kugelrohr for ~30 minutes at 150° C. and high vacuum to give 5.53 g (41.1% yield) of the title product as a clear nearly colorless oil.

Example 5.2

1,2-bis(1-bromooctyl)benzene (5.2)

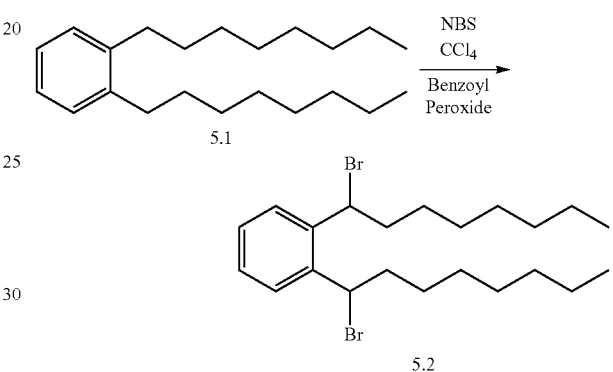

An oil bath is raised to 80° C. To a clean dry 100 cm³ round bottom flask is added a stir bar, 1.37 g (7.67 mmol, 2.30 eq) of N-bromosuccinimide, 1.01 g (3.34 mmol, 1.00 eq) of 1,2-dioctylbenzene (5.1) and 5.7 mg of benzoyl peroxide. The flask is fitted with a condenser, then capped and purged three times with nitrogen and vacuum. Carbon tetrachloride (20 cm³) is added by syringe and the reaction is dropped into the oil bath at 80° C. and allowed to stir at reflux overnight. The carbon tetrachloride is rotary evaporated, hexane is added, the mixture is sonicated, and the succinimide is removed by filtration. The hexane is then removed by rotary evaporation to give 1.59 g (quantitative) of title product as an oil and possible mixture of isomers. This material is used directly in the next reaction without further purification or other manipulation.

Example 5.3

Fullerene 5

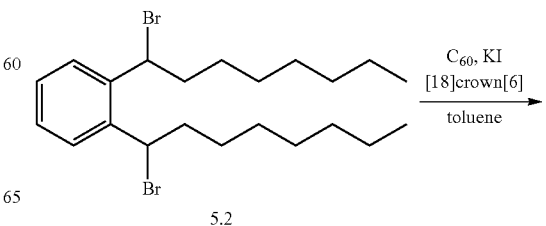

-continued

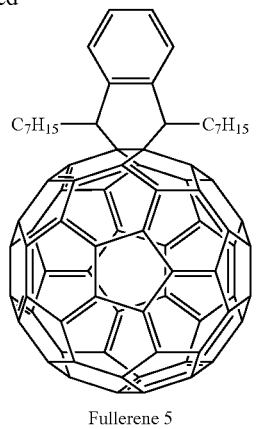

Fullerene 5

An oil bath is brought to 130° C. To a clean dry 2 dm³, two-neck, round bottom flask containing a stir bar is added 3.49 g (5.02 mmol, 1.45 eq) of $C_{60}$ fullerene, 2.40 g (14.45 mmol, 4.32 eq, 166.00 g/mol) of potassium iodide, 14.38 g (54.40 mmol, 16.26 eq) of [18]crown[6] and 1.5 dm³ of toluene. The round bottom is fitted with a condenser, sealed and purged three times with nitrogen and vacuum. The mixture is lowered into the oil bath and allowed to reach reflux. 1,2-Bis(1-bromooctyl)benzene (5.2) (1.54 g, 3.35 mmol, 1.00 eq) of the dibromide is then added by syringe in one portion in 50 cm³ of reagent grade toluene. The reaction is refluxed and stirred in the dark overnight after lowering the oil bath temperature to 125° C. After cooling, the reaction mixture is washed twice with 250 cm³ of 5% sodium hydroxide solution. After the washings the entire solution is filtered to give 454 mg of nearly pure, dry $C_{60}$. The filtrate is then washed twice with 250 cm³ of water, dried with magnesium sulfate, filtered, and toluene is removed by rotary evaporation. Purification is carried out completely by preparative intermediate pressure liquid chromatography using a column with Cosmosil Buckyprep material as the stationary phase (from Nacalai Tesque; pyrenylpropyl group bonded silica) and toluene as the mobile phase. Fractions containing high purity product are collected and combined, the toluene is removed using rotary evaporation, and samples are left in an oven overnight at 70° C. under reduced pressure to remove residual solvent. Fullerene 5 is isolated (580 mg, 17.0%) as a brown crystalline solid. Purity is confirmed at 99.76% by analytical HPLC using a column with Cosmosil Buckyprep material as the stationary phase (from Nacalai Tesque; pyrenylpropyl group bonded silica) and toluene as the mobile phase.

B) WORKING EXAMPLES

Example B1

Bulk Heterojunction Organic Photovoltaic Device (OPV) from Fullerene 1 and Fullerene 2

Organic photovoltaic (OPV) devices are fabricated on pre-patterned ITO-glass substrates (13 Ω/sq.) purchased from LUMTEC Corporation. Substrates are cleaned using common solvents (acetone, iso-propanol, deionized-water) in an ultrasonic bath. A conducting polymer poly(ethylene dioxythiophene) doped with poly(styrene sulfonic acid) [Clevios VPAI 4083 (H. C. Starck)] is mixed in a 1:1 ratio with deionized-water. This solution is filtered using a 0.45 µm filter before spin-coating to achieve a thickness of 20 nm. Substrates are exposed to ozone prior to the spin-coating process to ensure good wetting properties. Films are then annealed at 140° C. for 30 minutes in a nitrogen atmosphere where they are kept for the remainder of the process. Active material solutions (i.e. polymer+fullerene) are prepared to fully dissolve the solutes. Thin films are either spin-coated or blade-coated in a nitrogen atmosphere to achieve active layer thicknesses between 50 and 500 nm as measured using a profilometer. A short drying period follows to ensure removal of any residual solvent.

Typically, blade-coated films are dried at 70° C. for 2 minutes on a hotplate. For the last step of the device fabrication, Ca (30 nm)/Al(100 nm) cathodes are thermally evaporated through a shadow mask to define the cells. Current-voltage characteristics are measured using a Keithley 2400 SMU while the solar cells are illuminated by a Newport Solar Simulator at 100 mW·cm⁻² white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV devices are prepared wherein the photoactive layer contains a blend of a polymer 1 having the structure below and either oQDM-$C_{60}$ or Fullerene 1 or Fullerene 2 of Example 1 or 2, respectively, which is coated from a o-dichlorobenzene solution at a total solid concentration as shown in Table 1 below. The OPV device characteristics are shown in Table 1.

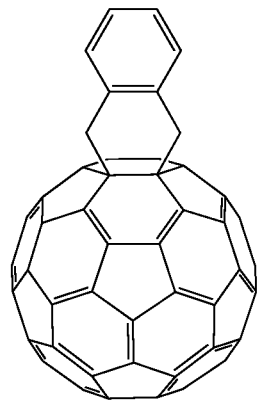

oQDM-$C_{60}$ oQDM-$C_{60}$ and its preparation are disclosed, for example, in Angewandte *Chemie* 1993, 105, 95-7.

Polymer 1

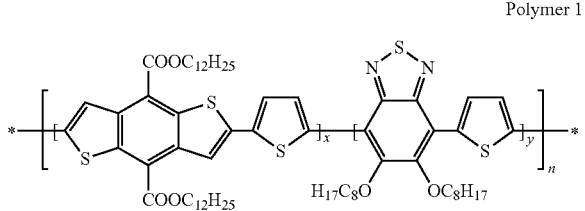

Polymer 1 and its preparation are disclosed in WO 2011/131280.

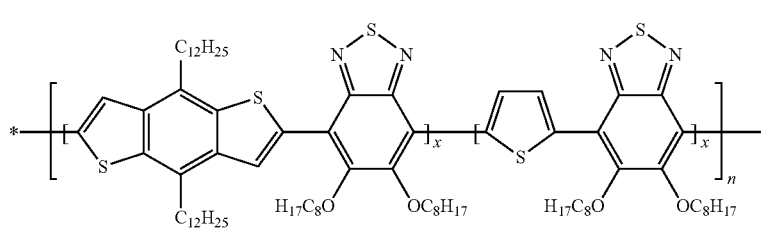

Polymer 2

Polymer 2 and its preparation are disclosed in WO 2013/135339.

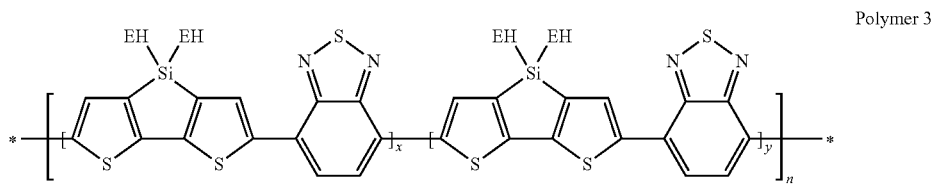

Polymer 3

Polymer 3 and its preparation are disclosed in U.S. Pat. No. 8,455,606 B2.

TABLE 1

Photovoltaic cell characteristics.

| Fullerene | Polymer | ratio Polymer:Fullerene | conc$^n$ mg · cm$^{-3}$ | Voc mV | Jsc mA · cm$^{-2}$ | FF % | PCE % |
|---|---|---|---|---|---|---|---|
| oQDM-C$_{60}$ | 1 | 1.00:2.00 | 30 | 860 | −8.33 | 32.9 | 2.35 |
| 1 | 1 | 2.00:3.00 | 30 | 876 | −9.28 | 61.8 | 5.03 |
| 1 | 1 | 1.00:3.00 | 30 | 860 | −6.49 | 57.7 | 3.23 |
| 2 | 1 | 2.00:3.00 | 30 | 810 | −2.49 | 43.5 | 0.88 |
| 2 | 1 | 1.00:3.00 | 30 | 773 | −3.10 | 48.8 | 1.17 |
| 3 | 1 | 2.00:3.00 | 30 | 840 | −6.84 | 63.3 | 3.63 |
| 3 | 1 | 1.00:3.00 | 30 | 580 | −4.47 | 40.6 | 1.06 |
| 4 | 1 | 2.00:3.00 | 30 | 860 | −9.55 | 58.3 | 4.79 |
| 4 | 1 | 1.00:3.00 | 30 | 860 | −8.28 | 63.1 | 4.49 |
| 4 | 2 | 2.00:3.00 | 30 | 964 | −6.37 | 35.5 | 2.19 |
| 4 | 3 | 2.00:3.00 | 30 | 687 | −9.60 | 41.3 | 2.73 |
| 4 | P3HT | 2.00:3.00 | 30 | 660 | −7.42 | 69.3 | 3.39 |
| 5 | 1 | 2.00:3.00 | 30 | 838 | −6.62 | 44.7 | 2.49 |

It can be seen that oQDM-C$_{60}$, which has lower solubility in common organic solvents, prohibits the formation of the suitable morphology to achieve good performance in an OPV device, compared to the C$_{60}$ fullerenes Fullerene 1, Fullerene 3, Fullerene 4 and Fullerene 5 according to the invention which shows significantly better performance.

Example 3

Solubility Examples

As control and enhancement of the solubility of fullerene derivatives used as n-phase material is an important aspect in many embodiments of the present invention, the solubility of Fullerene 1 and Fullerene 2 has been determined at room temperature (about 22° C.) in o-dichlorobenzene, in comparison to that of oQDM-C$_{60}$. The solvent o-dichlorobenzene is a common solvent for the deposition of active layers of OPV devices and also used in the working examples herein.

For this purpose, the following procedure for the determination of solubilities has been used.

As the determination of the concentration is based on the absorbance at 360 nm, a calibration curve is established first. Solutions of Fullerene 1, Fullerene 2 and oQDM-C$_{60}$ in o-dichlorobenzene at concentrations of 0.1 mg/cm$^3$ are prepared. Diluting fractions of the solutions further, additional solutions at concentrations of 0.02 and 0.004 mg/cm$^3$ are obtained, respectively. UV-vis spectra between 300 and 1100 nm have been measured and the absorbances at 360 nm recorded. Absorbance vs. concentration has been plotted for Fullerene 1 and Fullerene 2 respectively. Linear trend lines intercepting at (0,0) have been added and the slopes, to be used as response factors, recorded.

In order to assess solubilities, concentrated solutions, targeted to be saturated, of Fullerene 1 to 5 and, for comparison, oQDM-C$_{60}$ have been prepared. In more detail: 57 mg of Fullerene 1, 85 mg of Fullerene 2, 82.9 mg of Fullerene 3, 78.3 mg of Fullerene 4, 157 mg of Fullerene 5 and 46 mg of oQDM-C$_{60}$ have been added to 1 cm$^3$ of o-dichlorobenzene and stirred overnight with a magnetic stir bar. The solution was filtered through a 0.2 μm syringe filter and diluted with o-dichlorobenzene in order to reach concentrations suitable for the UV-vis spectrometer. UV-vis spectra of the resulting solutions are measured and the absorbances at 360 nm recorded.

Using the calibration curves described above and taking into account the dilution factors, the following solubilities in o-dichlorobenzene at room temperatures have been obtained:

oQDM-$C_{60}$: 5.8 mg/cm$^3$
Fullerene 1: 23 mg/cm$^3$
Fullerene 2: >85 mg/cm$^3$
Fullerene 3: 9.3 mg/cm$^3$
Fullerene 4: 45 mg/cm$^3$
Fullerene 5: 20 mg/cm$^3$ The value for Fullerene 2 is a minimum value as all material initially added has been dissolved and the solution may not have been saturated. Finally, it can be concluded that functionalization schemes, as described herein, allow for an unexpectedly pronounced increase of solubilities in a solvent pertinent for the preparation of OPV devices and other solvents and devices.

The invention claimed is:

1. A compound of formula I

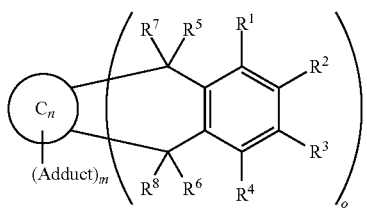

wherein $C_n$ is a fullerene composed of n carbon atoms, optionally with one or more atoms trapped inside, Adduct is a secondary adduct, or a combination of secondary adducts, appended to the fullerene $C_n$, m is the number of secondary adducts appended to the fullerene $C_n$, and is 0, an integer ≥1, or a non-integer >0, o is an integer ≥1, $R^1$ to $R^8$ independently of each other, denote H or a straight-chain, branched or cyclic alkyl group with 1 to 50 C atoms, in which one or more $CH_2$ groups are optionally replaced by —O—, —S—, —C(=O)—, —C(=S)—, —C(=O)—O—, —O—C(=O)—, —S(O)$_2$—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, or one or more $CH_2$ or $CH_3$ groups are replaced by a cationic group or an anionic group, and in which one or more H atoms are optionally replaced by F, Cl, Br, I or CN, or $R^1$ to $R^8$ denote a non-aromatic carbo- or heterocyclic group that is saturated or unsaturated, or an aryl or heteroaryl group, wherein each of the aforementioned cyclic groups has 3 to 20 ring atoms, is mono- or polycyclic, contains fused and/or unfused rings, and is optionally substituted by one or more groups $R^S$, $R^0$ and $R^{00}$ denote H or an optionally substituted carbyl or hydrocarbyl group with 1 to 40 C atoms, $Y^1$ and $Y^2$ are independently of each other H, F, Cl or CN, $R^S$ denotes halogen or a straight-chain, branched or cyclic alkyl moiety with 1 to 30 C atoms, in which one or more $CH_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, characterized in that in formula I at least one of $R^5$ and $R^7$ is different from H and at least one of $R^6$ and $R^8$ is different from H, and wherein those groups $R^5$, $R^6$, $R^7$ and $R^8$ which are different from H are selected from $C_1$-$C_{50}$ optionally substituted alkyl groups.

2. The compound of claim 1, wherein one or more of $R^1$, $R^2$, $R^3$, $R^4$, $R^5$, $R^6$, $R^7$ and $R^8$ denote H.

3. The compound of claim 1, wherein $R^5$ and $R^6$ are different from H and $R^7$ and $R^8$ denote H, or $R^7$ and $R^8$ are different from H and $R^5$ and $R^6$ denote H.

4. The compound according to claim 1, wherein one or more of $R^1$, $R^2$, $R^3$, $R^4$, $R^5$, $R^6$, $R^7$ and $R^8$ denote a straight-chain, branched or cyclic alkyl group with 1 to 50 C atoms, in which one or more $CH_2$ or $CH_3$ groups are replaced by a cationic or anionic group.

5. The compound according to claim 1, wherein n is 60, 70, 76, 78, 82, 84, 90, 94 or 96.

6. The compound according to claim 5, wherein n is 60.

7. The compound according to claim 5, wherein n is 70.

8. The compound according to claim 1, wherein m is 0, 1, 2 or 3.

9. The compound according to claim 8, wherein m is 1, 2 or 3.

10. The compound according to claim 8, wherein m is 0.

11. The compound according to claim 1, wherein the "Adduct" in formula I is selected from the following formulae

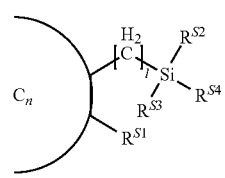

S-1

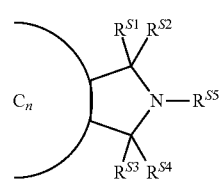

S-2

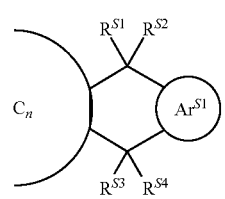

S-3

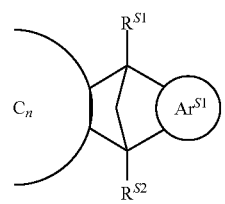

S-4

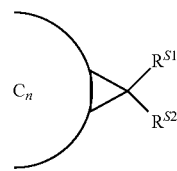

S-4

-continued

S-5

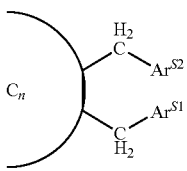

S-6

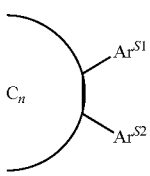

S-7

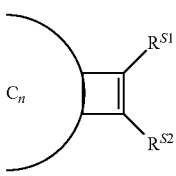

S-8

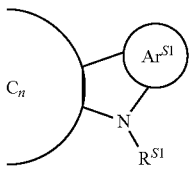

S-9

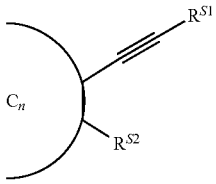

wherein
$R^{S1}$, $R^{S2}$, $R^{S3}$, $R^{S4}$ and $R^{S5}$ independently of each other denote H, halogen or CN, or have one of the meanings of $R^1$ as given in claim 1, or have one of the meanings of $Ar^{S1}$ as given below, $Ar^{S1}$ and $Ar^{S2}$ are independently of each other an aryl or heteroaryl group with 5 to 20 ring atoms, which is mono- or polycyclic, and which is substituted by one or more identical or different substituents $R^S$, wherein $R^S$ denotes halogen, or a straight-chain, branched or cyclic alkyl moiety with 1 to 30 C atoms, in which one or more CH$_2$ groups are optionally replaced by —O—, —S—, —C(O)—, —C(S)—, —C(O)—O—, —O—C(O)—, —S(O)$_2$—, —NR$^0$—, —SiR$^0$R$^{00}$—, —CF$_2$—, wherein R$^0$ and R$^{00}$ denote H or an optionally substituted carbyl or hydrocarbyl group with 1 to 40 C atoms.

12. The compound according to claim 1, which is selected from the following subformula

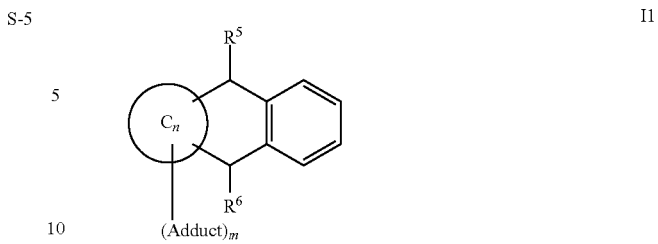

I1 wherein C$_n$, "Adduct", m, R$^5$ and R$^6$ are as defined in claim 1, with R$^5$ and R$^6$ being different from H.

13. The compound according to claim 1, which is selected from the following subformulae

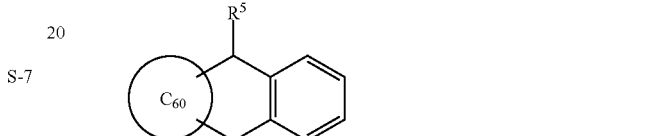

I1a1

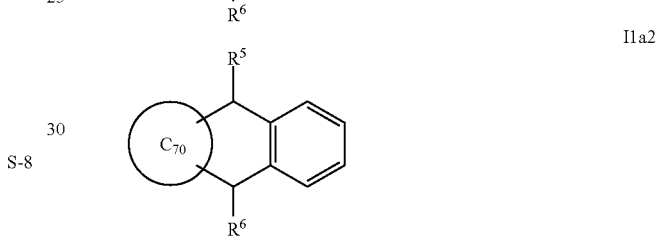

I1a2

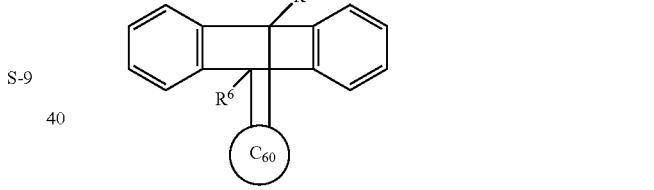

I2a1

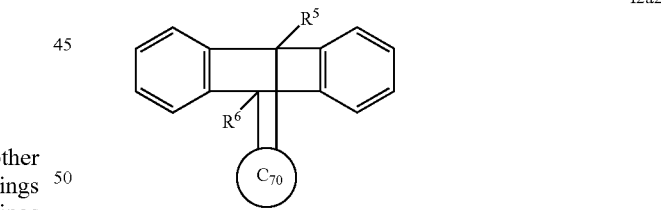

I2a2 wherein R$^5$ and R$^6$ denote independently of each other straight-chain or branched alkyl with 1 to 20 C atoms.

14. The compound according to claim 1 adapted for use as an electron acceptor or n-type semiconductor in a semiconducting material, organic electronic device, or component of an organic electronic device.

15. A composition comprising a compound according to claim 1.

16. The composition according to claim 15 adapted for use as a semiconducting, charge transport, electrically conducting, photoconducting, thermoelectric material or light emitting material, or in an optical, electrooptical, electronic, electroluminescent or photoluminescent device, or in a component of such a device or in an assembly comprising such a device or component.

17. A bulk heterojunction which comprises, or is being formed from, the composition of claim 15.

18. A composition which comprises one or more compounds according to claim 1 as electron acceptor or n-type semiconductor component, and further comprising one or more semiconducting compounds which have electron donor or p-type properties.

19. A composition which comprises one or more compounds according to claim 1 and one or more p-type organic semiconductor compounds selected from conjugated organic polymers.

20. A composition which comprises one or more compounds according to claim 1 and one or more compounds which are selected from compounds having one or more of a semiconducting, charge transport, hole transport, electron transport, hole blocking, electron blocking, electrically conducting, photoconducting and light emitting property.

21. A semiconducting, charge transport, electrically conducting, photoconducting or light emitting material, which comprises the compound according to claim 1.

22. A formulation comprising one or more compounds according to claim 1, and further comprising one or more organic solvents.

23. An optical, electrooptical, electronic, electroluminescent or photoluminescent device, or a component thereof, or an assembly comprising it, which is prepared using the formulation of claim 22.

24. An optical, electrooptical, electronic, electroluminescent or photoluminescent device, or a component of such a device, or an assembly comprising such a device, which comprises the compound according to claim 1.

25. The optical, electrooptical, electronic, electroluminescent or photoluminescent device of claim 24, which is selected from organic field effect transistors (OFET), organic thin film transistors (OTFT), organic light emitting diodes (OLED), organic light emitting transistors (OLET), organic photovoltaic devices (OPV), organic photodetectors (OPD), organic solar cells, thermoelectric device, laser diodes, Schottky diodes, photoconductors and photodetectors.

26. The device of claim 25, which is a bulk heterojunction (BHJ) OPV device or an inverted BHJ OPV device.

27. The component of an optical, electrooptical, electronic, electroluminescent or photoluminescent device of claim 24, which is selected from charge injection layers, charge transport layers, interlayers, planarising layers, antistatic films, polymer electrolyte membranes (PEM), conducting substrates and conducting patterns.

28. The assembly of claim 24, which is selected from integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

29. A method of making a compound of formula I according to claim 1 comprising:
reacting in one or more steps a precursor P-1 represented by P-1, wherein $R^1$ to $R^8$ have the meanings given above and below,

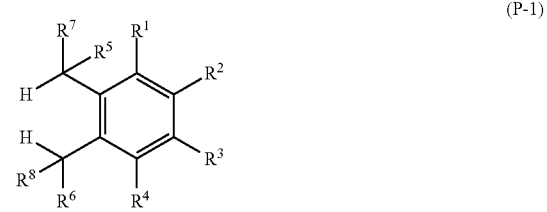

(P-1)

with at least one halogenating reagent to form a halogenated intermediate represented by P-2, wherein Hal denotes a halogen atom and $R^1$ to $R^8$ have the meanings given above and below,

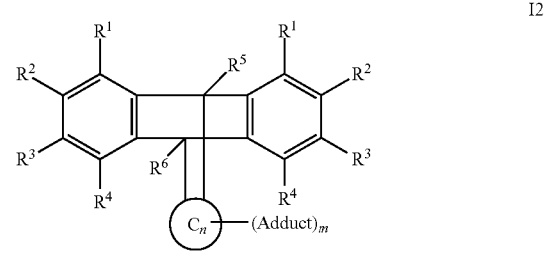

I2 and
reacting the intermediate P-2 in one or more steps with a fullerene compound represented by F-1 or F-2:

(F-1)

(F-2)

and, optionally, with a secondary adduct compound to form the compound of formula 1.

30. The method of claim 29, wherein the intermediate P-2 compound is directly reacted without purification with the fullerene compound.

31. The method of claim 29, wherein the intermediate P-2 compound is not contacted with untreated silica gel before being reacted with the fullerene compound.

* * * * *

UNITED STATES PATENT AND TRADEMARK OFFICE
CERTIFICATE OF CORRECTION

PATENT NO. : 9,502,658 B2
APPLICATION NO. : 14/257223
DATED : November 22, 2016
INVENTOR(S) : Edward A. Jackson et al.

Page 1 of 1

It is certified that error appears in the above-identified patent and that said Letters Patent is hereby corrected as shown below:

In the Claims

Column 92, Claim 29, between Lines 24 and 33, please delete:

" 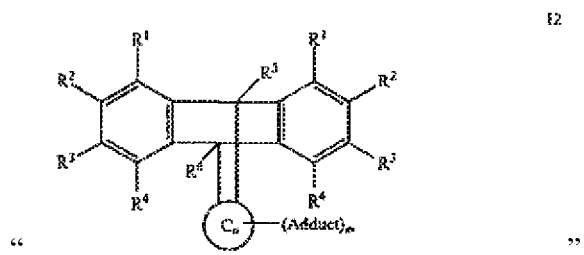 "

And insert: -- 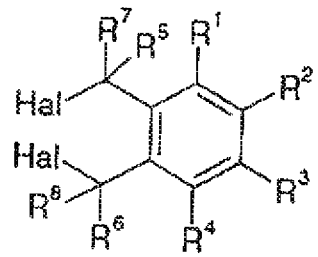 --

Signed and Sealed this
Twenty-fifth Day of April, 2017

Michelle K. Lee
*Director of the United States Patent and Trademark Office*